ись

United States Patent
Find

(10) Patent No.: US 11,013,191 B2
(45) Date of Patent: May 25, 2021

(54) METHOD FOR GROWING SOMATIC EMBRYOS OF CONIFERS INTO TREES

(71) Applicant: University of Copenhagen, Copenhagen (DK)

(72) Inventor: Jens Iver Find

(73) Assignee: UNIVERSITY OF COPENHAGEN, Copenhagen (DK)

( * ) Notice: Subject to any disclaimer, the term of this patent is extended or adjusted under 35 U.S.C. 154(b) by 0 days.

(21) Appl. No.: 16/628,929

(22) PCT Filed: Jun. 29, 2018

(86) PCT No.: PCT/EP2018/067664
§ 371 (c)(1),
(2) Date: Jan. 6, 2020

(87) PCT Pub. No.: WO2019/007854
PCT Pub. Date: Jan. 10, 2019

(65) Prior Publication Data
US 2020/0236884 A1  Jul. 30, 2020

(30) Foreign Application Priority Data
Jul. 7, 2017 (DK) .......................... PA 2017 00405

(51) Int. Cl.
*A01H 4/00* (2006.01)
*A01H 7/00* (2006.01)

(52) U.S. Cl.
CPC .............. *A01H 4/005* (2013.01); *A01H 4/008* (2013.01); *A01H 7/00* (2013.01)

(58) Field of Classification Search
CPC ................................ A01H 4/005; A01H 4/008
USPC ........................................................ 435/420
See application file for complete search history.

(56) References Cited

U.S. PATENT DOCUMENTS

| | | | |
|---|---|---|---|
| 5,187,092 A | 2/1993 | Uddin | |
| 5,731,204 A | 3/1998 | Rutter et al. | |
| 6,897,065 B1 | 5/2005 | Find | |
| 8,216,841 B2 * | 7/2012 | Nehra | A01H 4/005 435/422 |
| 2009/0280566 A1 | 11/2009 | Carpenter et al. | |

OTHER PUBLICATIONS

Vookova et al. "Effect of sucrose concentration, charcoal, and indole-3-butyric acid on germination of Abies numidica somatic embryos," Biologia Plantarum 44(2): 181-184, 2001.*

Carneros et al. "Plant regeneration in Stone pine (*Pinus pinea* L.) by somatic embryogenesis," Plant Cell Tiss Organ Cult (2009) 98: 165-178.*

Lamhamedi et al. "Epidermal transpiration, ultrastructural characteristics and net photosynthesis of white spruce somatic seedlings in response to in vitro acclimatization," Physiologia Plantarum 118:554-561,2003.*

Liu, "A Monograph of the Genus Abies," Department of Forestry, College of Agriculture, National Taiwan University, Dec. 1971, 4 pages total.

Farjon et al., "Classification Of Abies Miller(PINACEAE)", Notes RBG Edinb. vol. 46, No. 1, 1989, pp. 59-79 (21 pages).

Häggman et al., "Somatic embryogenesis of Scots pine: cold treatment and characteristics of explants affecting induction", Journal of Experimental Botany, vol. 50, No. 341, Dec. 1999, pp. 1769-1778 (10 pages).

Malabadi et al., "Plant Regeneration via Somatic Embryogenesis Using Secondary Needles of Mature Trees of *Pinus roxburghii* Sarg", International Journal of Botany, vol. 3, No. 1, 2007, pp. 40-47 (9 pages).

Nawrot-Chorabik, "Plantlet regeneration through somatic embryogenesis in Nordmann's fir (*Abies nordmanniana*", J. For. Res. vol. 27, No. 6, 2016, pp. 1219-1228 (10 pages).

Nawrot-Chorabik, "Somatic Embryogenesis in Forest Plants", Embryogenesis, InTech, Apr. 2012, pp. 423-446 (25 pages).

Nørgaard, "Somatic embryo maturation and plant regeneration in Abies nordmanniana Lk", Plant Science vol. 124, 1997, pp. 211-221 (11 pages).

Pullman et al., "Fraser fir somatic embryogenesis: high frequency initiation, maintenance, embryo development, germination and cryopreservation", New Forests, vol. 47, 2016, pp. 453-480 (28 pages).

Von Arnold et al., "Norway spruce as a model for studying regulation of somatic embryo development in conifers", Vegetative Propogation of Forest Trees, National Institute of Forest Science(NIFoS), Seoul, Korea, 2016, pp. 351-372 (22 pages).

Von Arnold et al., "Spruce Embryogenesis", Methods in Molecular Biology, Plant Embryogenesis, vol. 427, 2008, pp. 31-47 (17 pages).

* cited by examiner

*Primary Examiner* — Susan McCormick Ewoldt
(74) *Attorney, Agent, or Firm* — Birch, Stewart, Kolasch & Birch, LLP

(57) ABSTRACT

The present invention relates to a method for producing trees or wood from fully mature cotyledonary somatic embryos (SE) of conifer species within the genus *Abies* and to the use of plants thus obtained. The invention concerns a method for treating and growing somatic embryos under conditions that induce and stimulate root growth, that induce and stimulate shoot formation and increases the survival rate of the embryos, plantlets and emblings. The emblings can subsequently be grown into trees. Trees derived from somatic embryogenesis and grown according to the method of the invention are of a very homogeneous appearance and quality, which is preferred in the production of trees such as Christmas trees thereby reducing the wastage rate.

15 Claims, 23 Drawing Sheets

METHOD FOR GROWING SOMATIC EMBRYOS OF CONIFERS INTO TREES

FIELD OF THE INVENTION

The present invention is within the field of producing trees or wood wherein the trees are provided by somatic embryogenesis (SE). The trees are conifer trees within the genus *Abies*. The invention concerns a method for treating and growing somatic embryos under conditions that induce and stimulate root growth, that induce and stimulate shoot formation and increases the survival rate of the embryos and plantlets compared to previous attempts to produce *Abies* trees from somatic embryogenesis. The plantlets can subsequently be grown into trees and due to the genetic similarity obtained by using somatic embryos compared to trees obtained by random crosspollination the *Abies* trees derived from somatic embryogenesis are of a very homogeneous appearance and quality, which is preferred in the production of trees such as Christmas trees thereby reducing the wastage rate.

BACKGROUND

The commercial European Christmas tree market sums yearly to about 70 million trees, 35 million of these are Nordmann fir (*Abies nordmanniana*). Denmark is the leading exporting country supplying market share of 10 million Nordmann fir trees. Nordmanns fir has grown from being a niche product harvested in forest plantings to be an agricultural crop mainly produced on farmland. The market is getting more and more competitive due to the fact of an increasing production, in best a stable consumption, and a transition of the market from smaller retail lots to box-store sale of large quantities of trees. Furthermore, a structural change is ongoing leading to fewer, but larger growers—and very strong competition also enforced by dealing with highly professional buyers and a still scattered production of many growers.

Traditionally, seed sources used in the Christmas tree industry originates from stands in the natural distribution area of Nordmann fir, and thereby deploying a very broad and variable genetic material. This is in strong contrast to the fact, that the end product of a Christmas tree is characterized as an 'ideotype' or a set of 'ideotypes' depending on specific markets, but generally characterized by an uniform height growth, symmetric and dense branching, slightly upright branch angle and dark green needles oriented in a symmetric three-dimensional rounded structure on the twigs. Furthermore a set of adaptive characters are of importance for the production: survival and adaption to local growth conditions and climate, i.e. late flushing (to avoid late spring frost), resistance to low winter temperatures etc. to avoid bud damage causing dead buds and thereby lack of symmetry. Because the visual appearance of the Christmas tree is of such an importance damaging factors as insects, especially adelgids (sucking on needles causing yellowing) and fungi receives a lot of attention, and if possible, are avoided by applying pesticides. The dark green color of the tree is strongly related to nutrient content of the needles, and thereby to fertilization practice and specific local growth conditions.

Based on broad natural seed sources, the proportion of suitable individuals are too limited for positive economic revenue—when simply naturally grown. Therefore labor intensive tree shearing and trimming operations, growth regulation of leader length normally are applied together with fertilization, weed control and pesticides application. Cloning is therefore highly relevant, offering the opportunity to uniform the genetic material used for the Christmas tree production and potentially 'withhold' the desired combination of traits—seen in a minor proportion of the trees—and needed for high quality Christmas trees, and adaptive traits securing a low risk production, and potentially also lowering pest problems and pesticide use, and high economic revenue. Although not optimal combinations of traits can be achieved in the cloned material, the simple fact, that SE clones are expected to be more uniform in growth and phenology will be beneficial for field operations like leader length control (where for some chemicals a leader length of 10-18 cm is targeted at the first treatment), but also for side trimming, where newly emerged shoots from side branches is broken at a length of 2 cm, and timing is crucial to secure optimal bud formation on the trimmed twig and thereby the best visual appearance, and natural looking growth the following year.

Somatic embryogenesis in combination with cryopreservation and field testing for identifying the best individuals is potentially a very efficient tool.

Shortcutting the time and resources spent on formation of plants by using somatic embryogenesis instead of growing naturally produced seeds have long been applied in different plant species. However, it has not been easy in trees and especially in conifers, it has proven difficult to provide sufficient survival rates of both the somatic embryos and of any plantlets obtained from somatic embryogenesis. Moreover, the reasons for the low survival rates seem to vary between the different genera and to some extent also between families.

Nawrot-Chorabik (2016) disclosed a method comprising both the development of somatic embryos of Nordmann's fir as well as their maturation. According to this paper, root formation was induced by means of growth on a SH medium containing inter alia IBA, microelements, sucrose and phytagel. To induce shoot formation germination was carried out in diffuse, white LED light at a humidity elevated to 70% in a medium comprising sucrose.

Pullman et al. (2016) disclosed a method for improving *Abies fraseri* for Christmas tree production. Mature embryos were exposed to a period of cold storage of 1-2 months at 4° C., whereby a significantly better root growth was achieved.

US2009/0280566 disclosed a method of increasing germination and the frequency of viable somatic embryos from pines such as *Pinus* species produced in vitro. The method contains three steps and comprises a period of cold treatment at 0-10° C. for at least one week.

U.S. Pat. No. 5,731,204 described a method of producing pines from somatic embryos in *Pinus* trees and *Pinus* hybrids. Basically, the method consists of three steps: a) one step where somatic embryos are grown in a medium containing PEG, b) a period of cold storage of 2-12 weeks at 0-10° C., c) a further growth period in a growth medium containing sucrose. It is concluded to be essential that ABA and PEG are present in the medium in the growth period prior to the period of cold storage, and that the period of cold storage is decisive for overcoming the inhibiting effects of PEG on the germination.

Kartarzyna Nawrot-Chorabik (2012) described factors believed to increase root formation. It was further recommended that small rooted somatic embryos are transferred to growth under white LED light that is about 10 times lower in intensity than under natural conditions.

Malabadi and Nataraja (2007) applied a cold-pretreatment at 4° C. to induce the development of embryogenic tissue. As regards light-intensity it is mentioned that plantlets were placed in growth room under a 16 h photoperiod (50 μmol m-2 s-1).

Häggman et al. (1999) applied a cold-treatment of 14 days-2 months at 5° C. in connection with the treatment of cones, i.e. before the immature zygotic embryos were used for initiating embryogenic cultures. As regards the light-intensity during the development of the somatic embryos, the embryogenic cell masses were cultivated in the dark at 25±2° C., and during germination they were grown under a 16/8 h light/dark photoperiod (67-74 μE m-2 s-1) at 24° C.

Thus, until now, a complete satisfactory method for providing a sufficient number of fit plantlets derived from somatic embryogenesis in conifer trees of the *Abies* genera has been missing. Therefore, the majority of the Christmas tree production today is based on seeds that have been collected from uncontrolled pollinations deriving from approximately 35 year old trees, which is the age wherein most species within the genus *Abies* initiates seed production. The resulting trees show great differences in growth and appearance and approximately 30% of the trees are not suited for the production of Christmas trees. This will only become evident after 8-10 years of growth. In addition, pests and herbivores further reduce the production. Therefore, vegetative production from selected elite trees are beneficial in that all trees will have the genetic potential for the desired appearance and optionally improved growth.

It has until now proved difficult to obtain somatic embryos of the species within the *Abies* genus that develop both root and shoots sufficiently for the small plantlets to survive. The present method provides a solution to this problem in that it stimulates root formation by growing the mature somatic embryos at low temperatures for a period of time followed by growth in LED light and in a substrate that does not comprise a significant amount of a plant accessible carbohydrate source which stimulates the shoot formation.

SUMMARY OF THE INVENTION

The invention concerns a method for development of plants from fully mature somatic embryos by stimulating development and growth of roots and shoots in conifer somatic embryos with the aim of shortcutting the time and the investment needed for the vegetative propagation of a large number of conifers of a preferred genotype.

The method has proven to be of particular benefit in the development of somatic embryos from conifer trees of the *Abies* genus, particularly *Abies nordmanniana* (Nordmann fir). It is further expected that similar beneficial development will be obtained in other *Abies* species, species that are suitable for the production of Christmas trees and for cut greenery, particularly in *Abies bornmülleriana*.

The fully mature somatic embryos that serve as starting material to be grown according to the method of the present invention can be generated from a variety of tissues of either sexual origin such as immature mega gametophytes and excised zygotic embryos or from tissues of asexual origin such as vegetative shoot apices from aged trees. Fully mature *Abies* somatic embryos obtained from any method known in the art may be used for further development and growth by the method according to the present invention.

The method of the present invention comprises the following steps:

a) Subjecting somatic conifer embryos to 2-7° C. for 8-16 weeks b) Collecting the small plantlets from step (a) that have developed a root and growing said small plantlets in a substrate that does not comprise a significant concentration of a plant accessible carbohydrate source; at light intensities of 70-300 μmol/m²s; by use of LED light for at least 3 weeks c) Selecting the emblings obtained from step b) and growing these into plants The small plantlets obtained from step (b) are usually grown under these conditions for 4-8 weeks but can be grown under the conditions of step (b) for up to at least 3 months. In addition to inducing the root and shoot formation the survival rate of the somatic embryos are accordingly improved. Also, these growth conditions makes the emblings obtained after step (b) suitable for further growth under conditions that prevent dormancy when the plant are transferred to soil.

After the somatic embryos have been grown according to step a) and step b) of the method of the present invention, the emblings can be further grown in step c) under any suitable conditions for instance as plug plants grown either in the green house, nursery, or in the open for a period of time such as 1-2 years until the plants have obtained a suitable size for growing in the open such as in a field or forest until the desired stage for felling or cutting. Step c) includes any growth conditions suitable for growing the emblings obtained from step b) into plants of a desired size.

For many conifer species and many cell lines it has not been possible to regenerate plants by the methods known in the art. Using the method according to the present invention, the number of species and cell lines from which mature somatic embryos can be developed into emblings has increased significantly. Since the emblings obtained by the present method are of a higher quality, the continued growth of the emblings into plants has also been improved.

DETAILED DESCRIPTION OF THE INVENTION

The method of the present invention stimulates and improves growth of roots and shoots in fully mature conifer somatic embryos thereby shortcutting the time and the investment needed for the vegetative propagation of large numbers of conifers of a preferred genotype.

The method is suitable for the development of plants from fully mature somatic embryos of conifer trees of the *Abies* genus, including *Abies alba, Abies amabilis, Abies balsamea, Abies beshanzuensis, Abies bifolia, Abies borisiiregis, Abies bornmülleriana, Abies bracteata, Abies cephalonica, Abies chensiensis, Abies cilicica, Abies concolor, Abies delavayi, Abies densa, Abies duragensis, Abies equitrojani, Abies fabri, Abies fargesii, Abies fanjingshanensis, Abies firma, Abies flinckii, Abies forrestii, Abies fraseri, Abies guatemalensis, Abies hickelii, Abies holophylla, Abies homolepis, Abies kawakamii, Abies koreana, Abies lasiocarpa, Abies lowiana, Abies magnifica, Abies mariesii, Abies nebrodensis, Abies nephrolepis, Abies nordmanniana, Abies numidica, Abies pardei, Abies pindrow, Abies pinsapo, Abies procera (Abies nobilis), Abies recurvata, Abies religiosa, Abies sachalinensis, Abies sibirica, Abies spectabilis, Abies squamata, Abies veitchii, Abies vejarii, Abies yuanbaoshanensis, Abies ziyuanensis*, and any hybrids obtained from inter-species hybridization between any of the species of the *Abies* genus.

Members of the *Abies* genus are not always classified in the same way, for instance is *A. bornmülleriana* according to some classified as a sub-species rather than an independent species (Farjon and Rushfort, 1989, Liu 1971). The method according to the present invention will be suitable for any species or sub-species of the *Abies* genus. Also, the members of the *Abies* genus often hybridise between the species and/or sub-species. Hybridisation between species is particularly common between the European species of the *Abies* genus. The method according to the present invention will also be suitable for growing hybrids within members of the *Abies* species.

In one aspect, the method is suitable for the development of plants from fully mature somatic embryos from the European species of the *Abies* genus including: *Abies alba*, *Abies nebrodensis*, *Abies borisii-regis*, *Abies cephalonica*, *Abies nordmanniana*, *Abies bornmülleriana*, *Abies pinsapo*, *Abies numidica*, *Abies cilicica*, and hybrids obtained from inter-species hybridization between the European species of the *Abies* genus.

The method has proven to be particularly beneficial for the development of plants from fully mature somatic embryos of *Abies nordmanniana* (Nordmann fir) and *Abies bornmülleriana*.

The fully mature somatic embryos to be grown according to the method of the present invention can be generated from a variety of tissues of either sexual origin such as immature mega gametophytes and excised zygotic embryos or from tissues of asexual origin such as vegetative shoot apices from aged trees. Fully mature *Abies* somatic embryos obtained from any method known in the art may be used for further development and growth by the method according to the present invention. In a preferred embodiment, the somatic embryos are derived from excised zygotic embryos. Somatic embryos of *Abies* species can for instance be obtained as described in U.S. Pat. No. 6,897,065 and are suitable for being developed grown into plantlets according to the method of the present invention.

Plant regeneration through somatic embryogenesis in conifers generally consists of a number of consecutive steps. First, an embryogenic culture is initiated from an explant, which could be either an embryo, mature or immature, a seedling, buds or vegetative shoot apices from adult trees. This step is carried out on any suitable plant culture medium containing various plant growth regulators largely depending on the genus of the species in question. Typically, both auxin and cytokinin are included.

For continued proliferation, the initiated cultures are either subcultured on medium with the same composition as the induction medium or they are subcultured on medium with lower concentrations of plant growth regulators. At this stage, the proliferating cell masses consist of more or less well-differentiated immature somatic embryos, which morphologically correspond to a stage found in the developing seed in the early phase of seed development. Under optimal conditions, the somatic embryos do not undergo any further development during proliferation and mature embryos are thus not formed during this phase.

In order to obtain embryo maturation, the cultures need to be transferred to a plant culture medium, where-typically-auxin and cytokinin are omitted and abscisic acid (ABA) is included. In some cases, a short (1-3 weeks) transition step is included, during which the cell masses are cultured on plant culture medium devoid of plant growth regulators and optionally including activated charcoal. This phase is believed to facilitate subsequent maturation, due to the lower content or absence of auxin and cytokinin in the culture medium and their possible removal by activated charcoal.

A number of factors have been shown to have a general stimulatory effect on the frequency of embryo maturation and/or on the quality of the mature embryos formed. The most important factor is the naturally occurring plant growth regulator abscisic acid. This compound or analogues or derivatives thereof are included in almost all protocols for maturation of conifer somatic embryos.

Another factor of importance for the maturation process is the osmolality of the plant culture medium. Increasing this by adding a non-permeating osmoticum such as PEG-4000 (Polyethyleneglycol-4000) has been shown to improve especially the quality of the mature embryos. The improvement is suspected to be caused by an increased level of triacylglycerides in the mature embryos. Triacylglycerides are deposited in the cells during maturation of zygotic embryos and are used as an energy source for the germination. PEG-4000 or similar compounds are routinely incorporated into maturation media.

In the vast majority of conifers, sucrose is used as the sole carbohydrate source for the maturation step. However, there are reports that especially maltose may give superior results. This has been reported for *Pinus* spp (U.S. Pat. No. 5,187, 092) and for *Abies nordmanniana* (Nørgaard, 1997).

The inclusion of an auxin into the maturation medium, may stimulate both the number of mature somatic embryos formed, and their quality.

It is known that the ability of established embryogenic cultures to undergo maturation declines with their age. For some species, especially the members of *Pinus* genus the decline is very rapid, i.e. within months. Cultures from several other genera such as *Picea*, *Larix* and *Abies* are more long-term stable, but in most cases, some sort of decline is observed either as a reduced maturation frequency or as a requirement for longer maturation periods or higher concentration of maturation agents such as abscisic acid.

The development of somatic embryos from conifers is for instance described in von Arnold and Clapham 2008. A general drawing of the different stages of the early development of somatic embryos in conifers is shown in FIG. 1, which is a drawing of the development of Norway spruce (*Picea abies*) from von Arnold et al. 2016.

The somatic embryos to be grown into plants according to the method of the present invention should be fully mature cotyledonary embryos. Such embryos are in general 4-5 mm long, showing small cotyledons, typically 2-5 or more, and a radicle (root primordia), and having a diameter at the center of the stem of 1 mm. This stage corresponds to type 7 as shown in the drawing in FIG. 1 and in FIG. 2. Thus, somatic embryos of this stage is suitable for subjecting to the growth conditions of step (a) of the method of the invention as described further below.

The method of the present invention comprises the following steps:
  a) Subjecting fully mature cotyledonary somatic embryos to 2° C.-7° C. for 8-16 weeks
  b) Collecting the small plantlets from step (a) that have developed root and growing said small plantlets in a substrate that does not comprise a significant concentration of a plant accessible carbohydrate source; at light intensities of 70-300 μmol/m²s by use of LED light for at least 3 weeks
  c) Selecting the emblings obtained from step b) and growing these into plants Growing the fully mature cotyledonary somatic embryos under the conditions set out in step a) will induce and promote the development of the root.

In step a) above, the temperature may be 2° C., 3° C., 4° C., 5° C., 6° C. or 7° C. The temperature may also vary slightly such as from 3° C. to 7° C. during the treatment. The preferred temperature is a temperature range from 2° C. to 5° C. such as 2° C., 3° C. or such as the most preferred temperature of 4° C.

It is well known in the art that in practice, the exact temperature set in a certain growth facility such as a growth chamber, growth cabinet or growth room may vary slightly depending on the specific growth facility. Moreover, the uncertainty of temperature measurements depends on the specific means applied for measuring the temperature. Thus, the temperatures mentioned as applicable in step a) of the present method may in practice deviate slightly with up to ±0.5° C. or even up to ±1° C., depending on the specific growth facility and temperature measuring means.

In step a) above, the duration of subjecting the fully mature embryos to temperatures of 2-7° C. depends on the developmental rate of each individual embryo and on the specific *Abies* species. This treatment period generally ranges from 8 to 16 weeks, for most embryos the treatment period will be 12-14 weeks, preferably between 8 to 12 weeks, such as 9 to 11 weeks.

In step a) above, the fully mature embryos are preferably grown in the dark for the entire period. The plants may be grown in petri dishes comprising approximately 40 fully mature cotyledonary embryos per dish. The growth medium could be any suitable medium known in the art. An example of a suitable substrate is the substrate 51.21 as described in example 3 and 9.

After 8 weeks, the fully somatic embryos grown under the conditions of step (a) in the above mentioned method should be checked for root development. The somatic embryos are now small plantlets and the ones suitable for growth under the conditions in step (b) should be selected. As mentioned above, the appropriate time to move the small plantlets to step (b) depends on the species, clones/cell lines and also on the individual plantlet.

The somatic embryos/small plantlets should be checked for a period up until 14 or even 16 weeks in order to select and collect all small plantlets suitable for further growth. Most somatic embryos will have developed into small plantlets having the right developmental stage for transfer to step (b) after 8 to 12 weeks, such as 9 to 11 weeks. However, not all fully mature somatic embryos that have been subjected to 2-7° C. for 8 to 16 weeks according to step (a) will have developed a root after step (a) despite the beneficial treatment, but the number of somatic embryos/small plantlets that have survived and developed a root will be higher compared to fully mature somatic embryos that have not been grown under the conditions set out in step (a).

The small plantlets from step (a) that are selected after 8 to 16 weeks as being suitable for growth under the conditions set out in step (b) should have developed a root and cotyledons that are now 1-5 mm long and the hypocotyl should be about 5-15 mm long. Examples of plantlets of this stage are shown in FIG. 3.

In step (b), the selected small plantlets from step (a) having the applicable developmental stage are grown in a substrate that does not comprise a significant concentration of a plant accessible carbohydrate source; at light intensities of 70-300 $\mu mol/m^2 s$ by use of LED light in order to induce and promote shoot formation.

The growth conditions set out in step a) and b) improves the survival rate of fully mature somatic embryos that can be grown into viable emblings. Thus, the number of emblings that can be obtained from fully mature somatic embryos are greatly improved when the somatic embryos and subsequently the small plantlets are grown under the conditions set out in step a) and b).

In step (b), the sugar-free substrate could be any suitable substrate known in the art that does not comprise a significant concentration of a plant accessible carbohydrate source. Carbohydrate sources such as sugar, particularly sucrose, glucose, fructose, galactose, maltose, lactose, or starch are usually present or added to substrates and media for growing tissue cultures, embryos and plants. The carbohydrate source is added to the substrate to be taken up by the plant and used by the plant for growth and as an energy source for e.g. photosynthesis or respiration. The substrate or media used in step b) should not comprise such a carbohydrate source dedicated for the growth and energy source for the plants. Thus, any suitable substrate known in the art wherein the substrate is prepared in a version wherein the addition of one or more of a plant accessible carbohydrate source(s) usually present in the substrate is omitted may be used. An example of a suitable substrate is substrate 47.07 as described in Examples 4 and 10.

The small plantlets in step (b) should be grown under light from an LED source. Any LED source able to provide light intensities of 50-400 $\mu mol/m^2 s$ would be applicable. In relation to the present method, the 70-300 $\mu mol/m^2 s$ light intensities should be present/measured close to the cotyledons of the small plantlets. If the small plantlets are grown in boxes with a lid, the light intensities should be adjusted in order to remedy any loss of light due to the presence of the lid. The light intensities applied in step (b) could thus be 70 $\mu mol/m^2 s$, 100 $\mu mol/m^2 s$, 150 $\mu mol/m^2 s$, 200 $\mu mol/m^2 s$, 250 $\mu mol/m^2 s$ or 300 $\mu mol/m^2 s$. The most beneficial light intensity may vary between different species of the *Abies* genus but the more suitable light intensities are generally selected within the range 100 $\mu mol/m^2 s$-300 $\mu mol/m^2 s$, preferably within the range 150 $\mu mol/m^2 s$-250 $\mu mol/m^2 s$ such as 175 $\mu mol/m^2 s$-225 $\mu mol/m^2 s$.

In step (b) the small plantlets are optionally grown at 16 h light/8 h dark period, 18 h light/6 h dark period, 20 h light/4 h dark period, 22 h light/2 h dark period or at 24 hours light period. Most preferred is a 24 hours light period.

In step (b) the small plantlets can be grown at any suitable temperature such as from 10° C. to 25° C., most small plantlets would benefit from growing at temperatures from 12° C. to 18° C. such as at 15° C.

In step (b), the small plantlets can optionally be grown in transparent plastic boxes or in other suitable means. Preferably, the growth conditions are kept sterile. It has been found that when the small plantlets are grown in plastic boxes with a lid, it is beneficial that the box is not entirely air-tight. For instance, part of the lid may be removed or the lid may comprise one or more holes allowing air into the box and out of the box. The optimum relative air humidity may vary but for most small plantlets a relative air humidity of around 90% has proven to be suitable. It was found here that when growing the small plantlets in plastic boxes with a lid, keeping part of the lid area open, or having a filter allowing air movement in and out, corresponding to approximately 10-30% of the lid area increased the survival rate of the small plantlets significantly. The air movement could equally well be secured by other means than through a hole or filter in the lid for instance by securing air movement through the sides or the bottom of the box, and adjusted to the size of the box applied.

The duration of step (b) is at least three weeks until the plantlets have reached a stage (the embling stage) where they have developed new cotyledons, which also have turned darker green showing a 'normal' surface of a fully developed conifer needle. The total height of plantlet/embling above root varies and depends on the *Abies* species but will in most species be 8-22 mm. The length of the root is also variable but will in most *Abies* species be in the range of 1-30 mm. The minimum period required for most plants is 4 to 8 weeks. The small plantlets have then developed into emblings having new cotyledons, which also have turned darker green showing a 'normal' surface of a fully developed conifer needle. Total height of emblings above the root is generally 8-22 mm. The root length is variable between the emblings and species but is normally in the range of 1-30 mm. Examples of plants of this stage are shown in FIG. 4. Most of the small plantlets will have reached this embling stage within 4 to 8 weeks; the majority will have reached this stage after 6 weeks.

After the emblings has finalized growing under the conditions set out in step (b), they are ready for further development and growth into plants in step c). The emblings in step c) can be grown into plants under any suitable conditions known in the art. The emblings may initially be transferred to individual plugs and transferred to commercial nurseries and subsequently replanted when applicable until the plants has reached a size suitable for felling or greenery cutting for instance when the plants has reached a suitable size for a Christmas three.

In order to reduce the time, energy and other resources necessary for the plants to develop into entire trees, the plants obtained from the method described above i.e. plants that have successfully finalized step (a) and step (b) may subsequently be grown in step (c) under conditions that prevent the plants from entering the usual disrupting dormancy period of the growing season. The emblings obtained from step (b) by the present method has proven particularly receptive for growing under dormancy avoiding conditions.

In one embodiment of the present invention, the development of plants from fully mature cotyledonary somatic embryos of the *Abies* genus comprises:
  a) Subjecting the fully mature somatic embryos to 3-7° C. for 8-14 weeks
  b) Selecting the small plantlets obtained from step (a) that have developed a root and growing said small plantlets in a substrate that does not comprise a significant concentration of a plant accessible carbohydrate source; at light intensities of 150-250 µmol/m²s by use of LED light for 4 to 8 weeks
  c) Selecting the emblings obtained from step b) and growing these into plants In a more preferred embodiment of the present invention, the development of plants from fully mature cotyledonary somatic embryos of the *Abies* genus comprises:
  a) Subjecting the fully mature somatic embryos to 3-5° C. for 12 weeks
  b) Selecting the small plantlets obtained from step (a) that have developed a root and growing these in a substrate that does not comprise a significant concentration of a plant accessible carbohydrate source; at light intensities of 175-225 µmol/m²s by use of LED light for 4 to 8 weeks
  c) Selecting the emblings obtained from step b) and growing these into plants In a further preferred embodiment of the present invention, the development of plants from fully mature cotyledonary somatic embryos of the *Abies* genus comprises:
  a) Subjecting fully mature somatic embryos to 2° C.-5° C. for 9 to 11 weeks
  b) Selecting the small plantlets from step (a) that have developed a root and growing said small plantlets in a substrate that does not comprise a significant concentration of a plant accessible carbohydrate source; at LED light intensities of 175-225 µmol/m²s for 6 weeks
  c) Selecting the emblings obtained from step b) and growing these into plants In a further preferred embodiment of the present invention, the development of plants from fully mature cotyledonary somatic embryos of the *Abies* genus comprises:
  a) Subjecting the fully mature somatic embryos to 4° C. for 12 weeks
  b) Selecting the small plantlets obtained from step (a) that have developed a root and growing these in a substrate that does not comprise a significant concentration of a plant accessible carbohydrate source; at light intensities of 200 µmol/m²s by use of LED light for 4 to 8 weeks
  c) Selecting the emblings obtained from step b) and growing these into plants In a preferred embodiment, the fully mature conifer somatic embryos of the genus *Abies* are selected from the following *Abies* species: *Abies alba, Abies amabilis, Abies balsamea, Abies beshanzuensis, Abies bifolia, Abies borisii-regis, Abies bornmülleriana, Abies bracteata, Abies cephalonica, Abies chensiensis, Abies cilicica, Abies concolor, Abies delavayi, Abies densa, Abies duragensis, Abies equi-trojani, Abies fabri, Abies fargesii, Abies fanjingshanensis, Abies firma, Abies flinckii, Abies forrestii, Abies fraseri, Abies guatemalensis, Abies hickelii, Abies holophylla, Abies homolepis, Abies kawakamii, Abies koreana, Abies lasiocarpa, Abies lowiana, Abies magnifica, Abies mariesii, Abies nebrodensis, Abies nephrolepis, Abies nordmanniana, Abies numidica, Abies pardei, Abies pindrow, Abies pinsapo, Abies procera* (*Abies nobilis*), *Abies recurvata, Abies religiosa, Abies sachalinensis, Abies sibirica, Abies spectabilis, Abies squamata, Abies veitchii, Abies vejarii, Abies yuanbaoshanensis, Abies ziyuanensis*, and any hybrids obtained from inter-species hybridization between any of the species of the *Abies* genus.

In a further preferred embodiment, the fully mature conifer somatic embryos of the genus *Abies* is selected from *Abies alba, Abies nebrodensis, Abies borisii-regis, Abies cephalonica, Abies nordmanniana, Abies bornmülleriana, Abies pinsapo, Abies numidica, Abies cilicica*, and any hybrids obtained from inter-species hybridization between any of the European species of the *Abies* genus.

In particularly preferred embodiments, the fully mature somatic embryos are of *Abies nordmanniana* (Nordmann fir) or of *Abies* bornmülleriana and any hybrids obtained from inter-species hybridization between these species or between these species and any other species of the *Abies* genus.

In one embodiment, the fully mature somatic embryos such as somatic embryos of *Abies nordmanniana* (Nordmann fir) or of *Abies bornmülleriana* are derived from excised zygotic embryos. In a more preferred embodiment, the fully mature somatic embryos such as somatic embryos of *Abies nordmanniana* (Nordmann fir) or of *Abies bornmülleriana* are derived from excised zygotic embryos obtained by the method described in U.S. Pat. No. 6,897,065.

In one embodiment of the invention, the somatic embryos such as somatic embryos of *Abies nordmanniana* (Nordmann fir) or of *Abies bornmülleriana* are derived from excised zygotic embryos and when grown into plants the method comprises:
  a) Subjecting the fully mature somatic embryos to 3-7° C. for 8-14 weeks
  b) Selecting the small plantlets obtained from step (a) that have developed a root and growing these in a substrate that does not comprise a significant concentration of a plant accessible carbohydrate source; at light intensities of 100-300 μmol/m²s by use of LED light for at least three weeks c) Selecting the emblings obtained from step b) and growing these into plants In a more preferred embodiment of the invention, the somatic embryos such as somatic embryos of *Abies nordmanniana* (Nordmann fir) or of *Abies bornmülleriana* are derived from excised zygotic embryos and grown into plants by:

a) Subjecting the fully mature somatic embryos to 3° C.-5° C. for 12 weeks b) Selecting the small plantlets obtained from step (a) that have developed a root and growing these in a substrate that does not comprise a significant concentration of a plant accessible carbohydrate source; at light intensities of 150-250 μmol/m²s by use of LED light for 4-8 weeks c) Selecting the emblings obtained from step b) that have developed new cotyledons and growing these into plants In an aspect of the preferred embodiment of the invention, the somatic embryos such as somatic embryos of *Abies nordmanniana* (Nordmann fir) or of *Abies bornmülleriana* are derived from excised zygotic embryos and grown into plants by:

a) Subjecting fully mature somatic embryos to 2° C.-5° C. for 9 to 11 weeks b) Selecting the small plantlets from step (a) that have developed a root and growing said small plantlets in a substrate that does not comprise a significant concentration of a plant accessible carbohydrate source; at LED light intensities of 175-225 μmol/m²s for 6 weeks c) Selecting the emblings obtained from step b) and growing these into plants In a further preferred embodiment of the present invention, the somatic embryos such as somatic embryos of *Abies nordmanniana* (Nordmann fir) or of *Abies bornmülleriana* are derived from excised zygotic embryos and grown into plants by:

a) Subjecting the fully mature somatic embryos to 4° C. for 12 weeks b) Selecting the small plantlets obtained from step (a) that have developed a root and growing these in a substrate that does not comprise a significant concentration of a plant accessible carbohydrate source; at light intensities of 175-225 μmol/m²s by use of LED light for 4-8 weeks c) Selecting the emblings obtained from step b) and growing these into plants When used herein, "somatic cell culture" means a cell culture formed in vitro from vegetative (somatic) cells by mitotic division of cells. The somatic cell cultures can be generated from either sexually derived tissue (zygotic tissue) or from asexually/vegetative tissue. Examples of suitable tissues include: immature megagametophytes, excised zygotic embryos, vegetative shoot apices.

When used herein, "somatic embryo" means an embryo formed in vitro from vegetative (somatic) cells by mitotic division of cells. Early stage somatic embryos are morphologically similar to immature zygotic embryos. Somatic embryos can be generated from either sexually derived tissue (zygotic tissue) or from asexually/vegetative tissue. Examples of suitable tissues include: immature megagametophytes, excised zygotic embryos, vegetative shoot apices.

When used herein, "somatic embryogenesis" is the process of initiation and development of embryos in vitro from somatic cells and tissues.

When used herein, "fully mature somatic embryo" means a somatic embryo being approximately 4-5 mm long, showing small cotyledons, typically 2-5 or more, and a root primordia, and having a diameter at the center of the stem of approximately 1 mm. This stage corresponds to type 7 as shown in the drawing in FIG. 1 and in FIG. 2.

When used herein, "clone" means a group of genetically identical cell lines, SE's or plants obtained from the same zygotic tissue or from the same vegetative tissue.

When used wherein, "zygotic embryo" means an embryo derived from the sexual fusion of gametic cells or from seed embryo. In conifers, the zygotic embryo is placed in center of the seed surrounded by the megagametophyte (serving as nutritional media during germination)—being the female gametophyte.

When used herein, a "small plantlet" means a fully mature cotyledonary embryo that have further developed a root from the radicle, having cotyledons that are 1-5 mm long, and a hypocotyl which is about 5-15 mm long.

When used herein, "embling" means a small plantlet that have further developed into an embling having developed more cotyledons than the small plantlet, and the cotyledons have turned darker green showing a 'normal' surface of a fully developed conifer needle. The actual size may depend on the species, but in most species the total height of the embling above the root is 8-22 mm. The root length is variable but generally in the range of 1-30 mm.

When used herein, a "well developed embling" or "good embling" means an embling (as described above) that has further grown for 6-8 weeks, having at least one rosette of mostly green needles.

When used herein, somatic embryos having "developed a root" means that the fully mature somatic embryo has developed a clearly visible root from the radicle.

When used herein, "radicle" means tissue that has developed from the root primordia of a fully mature somatic embryo. The radicle is the early developmental stage of the root, developing at the lower end of the hypocotyl.

When used herein, "hypocotyl" means that portion of the stem below the cotyledons in a plant embryo, which eventually bears the roots.

When used herein, "cotyledons" means the first leaves of the somatic embryo which forms the first photosynthetic leaves. "New cotyledons" means additional cotyledons that has developed subsequent to the cotyledons present in the fully mature somatic embryo. In relation to the method of the present invention, "new" cotyledons" are any and all of the cotyledons developed while the fully mature cotyledonary embryos are subjected to step (a), i.e. 2-7° C. for 8-16 weeks.

When used herein, "root" means tissue that has developed from the radicle.

When used herein, "shoot" refers to either to 1) the aerial part of the embling that has developed from the small plantlet. In relation to the method of the present invention, this meaning of "shoot" refers to the aerial part of the plant that develops while the small plantlets are subjected to step (b), i.e. while growing the small plantlets in a substrate that does not comprise a significant concentration of a plant accessible carbohydrate source; at light intensities of 70-330 μmol/m²s by use of LED light for at least three weeks. Alternatively, the term "shoot" refers to 2) any new growth of the aerial parts of an embling, a small plant or of a plant. These parts include the stem, young branches, leaves and buds. In relation to the method of the present invention, this meaning of the term "shoot" is any development and growth of the aerial parts of the embling, small plant or plant while grown in step (c) i.e. under any suitable conditions known in the art including the plug stage and growing in commercial nurseries, the stages where the plants are optionally replanted and grown in the open such as in a field or in a forest until the plants has reached a size suitable for felling or greenery cutting for instance when the plants has reached a suitable size for a Christmas three.

When used herein, "bud" means a condensed rudimentary shoot. The bud is a compact body having an axis with a delicate growing point, nodes and very short unexpanded internodes and closely crowded young leaves.

When used herein, "plant accessible carbohydrate source" means any carbohydrate source, such as a monosaccharide, disaccharide, oligosaccharide or polysaccharide including sugars such as sucrose, glucose, fructose, galactose, maltose, lactose, or starch which can be taken up by the plant and used by the plant for growth as a carbon and energy source for e.g. photosynthesis or respiration. "A significant concentration" of a plant accessible carbohydrate source means that a carbohydrate source has been added to the media with the purpose of adding a carbohydrate source at a concentration wherein it can be taken up by the plants and used as a carbon or energy source for growth, photosynthesis or respiration.

When used herein, "sugar-free" substrate means any substrate or media that does not comprise a significant concentration of a plant accessible carbohydrate.

When used herein "substrate" and "media" are used interchangeably.

When used herein, "light intensities" refers to the light intensity measured as a photosynthetic photon flux (in the wave band 400-700 nm) in $\mu E/m^2s$ (micro Einstein per square meter and second) or in $\mu mol/m^2s$ (micro moles per square meter and second). These photosynthetic photon flux units correspond to each other, and can be used interchangeably. The light intensities may be measured with any standard equipment for measuring PAR (Photosynthetically Active Radiation), such as a Li-Cor Li250a Lightmeter and Licor quantum censor.

The present invention relates to the following aspects:

1. Method for development of plants from fully mature somatic embryos of the genus *Abies* comprising:
   a) Subjecting fully mature somatic embryos to 2° C.-7° C. for 8-16 weeks
   b) Selecting the small plantlets obtained from step (a) that have developed a root and growing said small plantlets in a substrate that does not comprise a significant concentration of a plant accessible carbohydrate source; at LED light intensities of 70-300 $\mu mol/m^2s$ for at least 3 weeks
   c) Selecting the emblings obtained from step b) and growing these into plants
2. Method according to aspect 1 wherein said temperature in step a) is 2° C.-5° C.
3. Method according to aspect 1 wherein said temperature in step a) is 3° C.-5° C.
4. Method according to any of aspects 1 to 3 wherein said temperature in step a) is 4° C.
5. Method according to any of aspects 1 to 4 wherein the fully mature embryos in step a) are subjected to said temperature for 9 to 11 weeks
6. Method according to any of aspects 1 to 4 wherein the fully mature embryos in step a) are subjected to said temperature for 12 weeks
7. Method according to any of aspects 1 to 6 wherein said LED light intensities applied in step b) are 150-250 $\mu mol/m^2s$
8. Method according to aspect 7 wherein said LED light intensities in step b) are 175-225 $mol/m^2s$
9. Method according to any of aspects 1 to 8 wherein said plantlets in step b) are grown in a substrate that does not comprise a significant concentration of a plant accessible carbohydrate source; at said LED light intensities for 4 to 8 weeks
10. Method according to aspect 9 wherein said plantlets in step b) are grown in a substrate that does not comprise a significant concentration of a plant accessible carbohydrate source; at said LED light intensities for 6 weeks
11. Method according to aspect 1 comprising:
    d) Subjecting fully mature somatic embryos to 2° C.-5° C. for 9 to 11 weeks
    e) Selecting the small plantlets from step (a) that have developed a root and growing said small plantlets in a substrate that does not comprise a significant concentration of a plant accessible carbohydrate source; at LED light intensities of 175-225 $\mu mol/m^2s$ for 6 weeks
    f) Selecting the emblings obtained from step b) and growing these into plants
12. Method according to aspect 1 comprising:
    a) Subjecting fully mature somatic embryos to 3° C.-7° C. for 12 weeks
    b) Selecting the small plantlets from step (a) that have developed a root and growing said small plantlets in a substrate that does not comprise a significant concentration of a plant accessible carbohydrate source; at LED light intensities of 175-225 $\mu mol/m^2s$ for 6 weeks
    c) Selecting the emblings obtained from step b) and growing these into plants
13. Method according to any of aspects 11 to 12 comprising:
    a) Subjecting fully mature somatic embryos to 4° C. for 12 weeks
    b) Selecting the small plantlets from step (a) that have developed a root and growing said small plantlets in a substrate that does not comprise a significant concentration of a plant accessible carbohydrate source; at LED light intensities of 200 $\mu mol/m^2s$ for 6 weeks
    c) Selecting the emblings obtained from step b) and growing these into plants
14. Method according to any of aspects 1 to 13 wherein said small plantlets in step (b) are grown in transparent boxes that allow aeration of said small plantlets
15. Method according to aspect 14 wherein said transparent box comprises a lid having a hole of 10-30% of the total area of the lid
16. Method according to any of aspects 1 to 15 wherein said somatic embryos of the genus *Abies* is selected from: *Abies alba, Abies amabilis, Abies balsamea, Abies beshanzuensis, Abies bifolia, Abies borisii-regis, Abies bornmülleriana, Abies bracteata, Abies cephalonica, Abies chensiensis, Abies cilicica, Abies concolor, Abies delavayi, Abies densa, Abies duragensis, Abies fabri, Abies fargesii, Abies fanjingshanensis, Abies firma, Abies flinckii, Abies forrestii, Abies fraseri, Abies guatemalensis, Abies hickelii, Abies holophylla, Abies homolepis, Abies kawakamii, Abies koreana, Abies lasiocarpa, Abies lowiana, Abies magnifica,*

*Abies mariesii, Abies nebrodensis, Abies nephrolepis, Abies nordmanniana, Abies numidica, Abies pardei, Abies pindrow, Abies pinsapo, Abies procera (Abies nobilis), Abies recurvata, Abies religiosa, Abies sachalinensis, Abies sibirica, Abies spectabilis, Abies squamata, Abies veitchii, Abies vejarii, Abies yuanbaoshanensis, Abies ziyuanensis* and any hybrids obtained from inter-species hybridization between any of these species of the *Abies* genus 17. Method according to any of aspects 1 to 16 wherein said somatic embryos of the genus *Abies* is selected from: *Abies alba, Abies nebrodensis, Abies borisii-regis, Abies cephalonica, Abies nordmanniana, Abies bornmülleriana, Abies pinsapo, Abies numidica, Abies cilicica* and any hybrids obtained from inter-species hybridization between any of these species or with other species of the *Abies* genus 18. Method according to aspect 17 wherein said somatic embryos of the genus *Abies* is selected from: *Abies nordmanniana* or *Abies bornmülleriana* and any hybrids obtained from inter-species hybridization between any of these species or with other species of the *Abies* genus 19. Use of plants obtained from a method according to any of aspects 1 to 18 for growing trees 20. Use of plants obtained from a method according to any of aspects 1 to 18 for the production of Christmas trees 21. Use of plants obtained from a method according to any of aspects 1 to 18 for the production of trees and cut greenery

Figure 1:
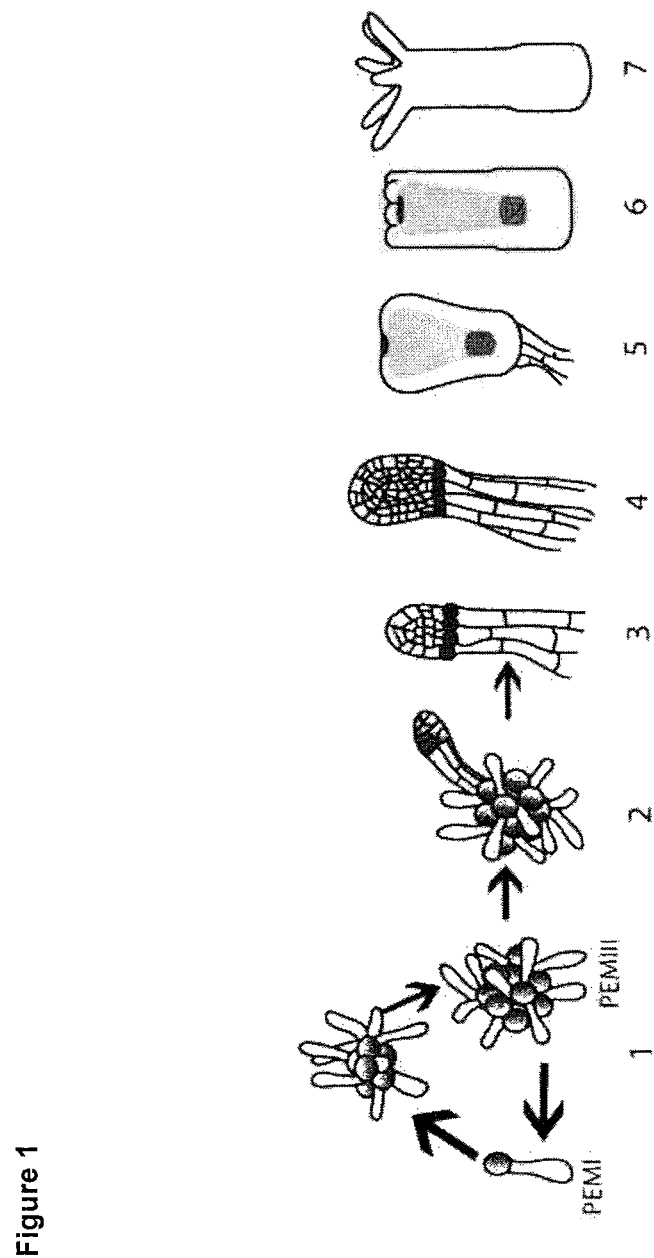
FIG. 1:
A drawing of the different stages of the early development of somatic embryos in Norway Spruce from von Arnold et al. 2016. The developmental stages of Norway spruce is similar to the developmental stages in other conifers and is often used as a "model system".

Three-dimensional graph showing the percentage of the accumulated rooted embryos as a function of rooting temperature and as a function of the number of weeks growth until rooting, when growing fully mature embryos of *Abies nordmanniana* and *Abies bornmülleriana* in dark at 2° C., 4° C., 5° C., 8° C., 10° C., 15° C. or 20° C., respectively, for 8, 9, 10 or 11 weeks.

FIG. 14:

Graph showing the accumulated percentage of embryo rooting for selected clones of *Abies nordmanniana* and *Abies bornmülleriana* as a function of the number of weeks subjected to growth in dark at 2° C., 4° C., 5° C., 8° C., 10° C., 15° C. or 20° C. for 8, 9, 10 or 11 weeks, respectively.

FIG. 15:

Diagram showing the percentage of rooted embryos as a function of the initial embryo quality score for the total number of rooted embryos obtained after growth in dark at 2° C., 4° C., 5° C., 8° C., 10° C., 15° C. or 20° C. for 8, 9, 10 or 11 weeks and for the good embryos obtained after growth in dark at 2° C., 4° C., 5° C., 8° C., 10° C., 15° C. or 20° C. for 8, 9, 10 or 11 weeks and subsequently grown in white LED light of 50, 100, 150, 200, 250, 300 or 400 $\mu$mol/m$^2$s for 8 weeks at 15° in 24 h light periods followed by additional growth for 8 weeks at 25° C. in white LED light of 175-195 $\mu$mol/m$^2$s in 24 h light periods.

FIG. 16:

Graph showing the percentage of rooted embryos subjected to growth in dark at 2° C., 4° C., 5° C., 8° C., 10° C., 15° C. or 20° C. for 8 to 11 weeks for selected clones of *Abies nordmanniana* and *Abies* bornmülleriana as a function of the initial embryo quality score.

FIG. 17:

Graph showing the percentage of rooting of *Abies nordmanniana* and *Abies bornmülleriana* embryos of different embryo quality scores as a function of the rooting temperature applied when growing the mature embryos in the dark at 2° C., 4° C., 5° C., 8° C., 10° C., 15° C. or 20° C., respectively, for 8 to 11 weeks.

FIG. 18:

Graph showing the number of cotyledons in emblings of *Abies nordmanniana* and *Abies bornmülleriana* as a function of $\mu$mol/m$^2$s LED light intensity after growing at white LED light of 50, 100, 150, 200, 250, 300 or 400 $\mu$mol/m$^2$s, respectively, for 8 weeks at 15° in 24 h light periods following initial growth in the dark at 2° C., 4° C., 5° C., 8° C., 10° C., 15° C. or 20° C., for 8 to 11 weeks.

FIG. 19:

Graph showing the length in mm of cotyledons in emblings of *Abies nordmanniana* and *Abies bornmülleriana* as a function of $\mu$mol/m$^2$s LED light intensity after growing at white LED light of 50, 100, 150, 200, 250, 300 or 400 $\mu$mol/m$^2$s, respectively, for 8 weeks at 15° in 24 h light periods following initial growth in the dark at 2° C., 4° C., 5° C., 8° C., 10° C., 15° C. or 20° C., for 8 to 11 weeks.

FIG. 20:

Graph showing the percentage of dead emblings of *Abies nordmanniana* and *Abies bornmülleriana* as a function of $\mu$mol/m$^2$s LED light intensity after growing at white LED light of 50, 100, 150, 200, 250, 300 or 400 $\mu$mol/m$^2$s, respectively, for 8 weeks at 15° in 24 h light periods followed by 8 weeks of growth in plugs at 25° C. with an average light intensity of 175-195 $\mu$mol/m$^2$s in 24 h light periods; following initial growth of the fully mature embryos in the dark at 2° C., 4° C., 5° C., 8° C., 10° C., 15° C. or 20° C., for 8 to 11 weeks.

FIG. 21:

Graph showing the percentage of good emblings of *Abies nordmanniana* and *Abies bornmülleriana* as a function of $\mu$mol/m$^2$s LED light intensity after growing at white LED light of 50, 100, 150, 200, 250, 300 or 400 $\mu$mol/m$^2$s, respectively, for 8 weeks at 15° in 24 h light periods followed by 8 weeks of growth in plugs at 25° C. in white LED light with an average light intensity of 175-195 $\mu$mol/m$^2$s in 24 h light periods; following initial growth of the fully mature embryos in the dark at 2° C., 4° C., 5° C., 8° C., 10° C., 15° C. or 20° C., for 8 to 11 weeks.

FIG. 22:

Three-dimensional graph showing the percentage of successful good emblings obtained from the total of fully mature embryos of *Abies nordmanniana* and *Abies bornmülleriana* obtained from growing the fully mature embryos in the dark at 2° C., 4° C., 5° C., 8° C., 10° C., 15° C. or 20° C., respectively, for 8 to 11 weeks followed by growth at white LED light of 50, 100, 150, 200, 250, 300 or 400 $\mu$mol/m$^2$s, respectively, for 8 weeks at 15° in 24 h light periods and additional growth for 8 weeks at 25° C. in white LED light of 175-195 $\mu$mol/m$^2$s in 24 h light periods; as a function of rooting temperature and LED light intensity $\mu$mol/m$^2$s.

FIG. 23:

Three-dimensional graph showing the percentage of successful good emblings obtained from the total of fully mature embryos of *Abies nordmanniana* and *Abies bornmülleriana* obtained from growing the fully mature embryos in the dark at 2° C., 4° C., 5° C., 8° C., 10° C., 15° C. or 20° C., respectively, for 8 to 11 weeks followed by growth at white LED light of 50, 100, 150, 200, 250, 300 or 400 $\mu$mol/m$^2$s, for 8 weeks at 15° in 24 h light periods; and additional growth for 8 weeks at 25° C. in white LED light of 175-195 $\mu$mol/m$^2$s in 24 h light periods as a function of rooting temperature and initial embryo quality score.

EXAMPLES

Example 1: Preparation of Somatic Embryos of *Abies nordmanniana*

Cones of *Abies nordmanniana* was collected from Ambrolauri, Georgian republic and cleaned and rinsed in water and disinfected with fungicide and ethanol. The cones were then stored at 5° C. for up to 60 days.

The seeds were then isolated from the cone by breaking the cone into pieces and collecting the seeds. The seeds were placed in a 35% hydrogen peroxide solution diluted 1:10 for 3-5 minutes while stirring. The seeds were then removed to a mild Presept® solution (1 tablet, 0.5 g, comprising troclosene sodium in 1 liter of water and two drops of detergent (Tween)) for 24 hours while ensuring access to oxygen to the solution by stirring. The seeds were rinsed in 70% ethanol for 3 minutes. This will also separate vital seeds from dead seeds; the vital seeds will sink whereas the dead seeds flow. Only the vital seeds were collected for further processing. The vital seeds were removed to a Precept solution (1 tablet in 0.5 L sterile water and 3-4 drops of detergent (Tween)) and placed on a shaker for 10 minutes. The seeds were then rinsed 3 times in sterile water under sterile conditions. If seeds have been stored for a long time or if they appear unclean, the can be briefly immersed into 96% ethanol and flamed.

The cleaned seeds where cut open and the seed embryo removed. Each embryo was placed in a petri dish comprising growth medium 29.4 in order to initiate the somatic cell culture. The embryo and the initiating culture were kept and grown in dark at 20° C. for 8-12 weeks until sufficient culture was available. Then the cultures were grown at 20° C. in the dark for 10 to 16 more weeks, and re-placed on fresh medium every second week.

Medium 29.4: 1 Liter

| | |
|---|---|
| H2O | 200 ml |
| BLG - RAT | 200 ml |
| BAP | 5.0 ml |
| BLG amino | 25 ml* |
| Sucrose | 10 g |
| Water up to | 975 ml¤ |
| Conductivity of solution¤ | 1.241-1.371 mS |
| pH | 5.7 |
| Phytagel | 1.8 g |

*Added after autoclaving

¤conductivity is measured in the solution of 975 ml, containing BLG-RAT, BAP and sucrose, after being set to pH 5.7

Recipes Used to Provide Medium 29.4

| | | | |
|---|---|---|---|
| BLG-Rat 200 ml | BLG 29 makro 500 ml | KNO3 | 1.000 g |
| | | KCL | 7.450 g |
| | | MgSO4 7H2O | 3.200 g |
| | | KH2PO4 | 1.700 g |
| | | CaCl2 2H2O | 4.400 g |
| | | H2O topped to | 1000 ml |
| | BLG 29 mikro/MS 7 5 ml | UNDER STAM 10 ml | CuSO4 5H2O 0.025 g |
| | | | CoCl2 6H2O 0.025 g |
| | | | H2O topped to 100 ml |
| | | H3BO3 | 0.62 g |
| | | MnSO4 H2O | 1.69 g |
| | | ZnSO4 7H2O | 0.86 g |
| | | KI | 0.083 g |
| | | Na2MoO4 2H2O | 0.025 g |
| | | H2O topped to | 100 ml |
| | FE EDTA 25.0 ml | FeSO4, 7H2O | 5.560 |
| | | Na2EDTA, 2H2O | 7.450 g |
| | | Cas no 6381-92-6 | |
| | | H2O topped to | 1000 ml |
| | DCR-2 10.0 ml | Thiamine-HCl | 0.100 g |
| | | Pyridoxine HCl | 0.050 g |
| | | Nicotinic Acid | 0.050 g |
| | | Glycine | 0.200 g |
| | | H2O topped to | 100 ml |
| | Inositol 1.000 g | | |
| | H2O topped to 2000 ml | | |
| BAP 5 ml | BAP | 0.0225 g | |
| | Cas no 1214-39-7 | | |
| | 1.0N KOH | 1.4 ml | |
| | H2O topped to | 100 ml | |
| BLG amino 25 ml | L-glutamin | 29.000 g | |
| | L-asparagin | 2.000 g | |
| | Barnsteadwater | 800 ml | |
| | H20 topped to | 1000 ml | |
| Sucrose | 10 g | | |
| H20 | 975 ml | | |
| Phytagel | 1.8 g | | |

Samples of the somatic cell culture can optionally be prepared for cryopreservation or be used directly for embryo development and maturation.

If the samples were cryopreserved, approximately 2 gram of tissue from one specific genotype were placed in a sterile bottle and 20 g of medium 29.4 was added, and 1 ml Sorbitol. The cultures were placed on a shaker providing constant agitation for adequate aeration for 24 hours at 20° C. and 1 ml sorbitol was added. After 48 hours, samples were placed at 0° C. for at least 30 min. Then, 1 ml DMSO was added to each bottle. The solution were divided into 12 tubes and slowly frozen from 0.5° C. to −35° C. before being transferred to a cryo-tank at minus 180° C.

When applicable, the somatic cell cultures were thawed and the development of somatic embryos was initiated.

The samples were thawed in 40° C. water, disinfected in ethanol and poured onto filter paper in a petri dish with medium 29.4. After 1 hour the filter papers with cultures were moved to a new petri dish with medium 29.4, and again after 18 hours the filter papers with cultures were placed in a new petri dish comprising a growth medium, such as medium 29.4.

The cultures are grown at 20° C. and the viability of the cultures are checked every $2^{nd}$ week. After 6 weeks, viable cultures are selected for embryo development and maturation. Every $2^{nd}$ week cultures were moved onto fresh medium 29.4. After another 6-8 weeks the cultures were ready.

Example 2: Embryo Development and Maturation of *Abies nordmanniana*

Somatic cell cultures from two different genotypes of *Abies nordmanniana* obtained from example 1 were selected for embryo development and maturation.

For each sample of somatic cell culture, 4 g of culture were added to 100 g 29.4 medium and blended for 25 seconds. The samples were then left for 30 minutes and any surplus liquid was removed until 30 ml. One ml of the blend was pipetted onto filter paper in a petri dish comprising 15 ml 49.53 medium.

Medium 49.53: 1 Liter

| | |
|---|---|
| BLG - RAT | 200 ml |
| ABA | 30 ml* |
| BLG-Amino | 25 ml* |
| PEG-4000 | 50 g** |
| Maltose | 45 g** |
| Water topped to | 445 ml** |
| Water up to | 500 ml¤ |
| pH | 5.7 |

| | |
|---|---|
| Conductivity of solution¤ | 2.39-2.65 mS |
| Phytagel | 1.8 g |

*Added after autoclaving

**PEG/the sugar, respectively, is mixed and autoclaved alone in the applied amount of water. The RAT-media can be obtained from common distributors such as Duchefa Biochemie.

¤conductivity is measured in the solution of 500 ml, containing BLG-RAT, after being set to pH 5.7

Recipes Used to Provide Medium 49.53

| | | | |
|---|---|---|---|
| BLG-Rat 200 ml | BLG 29 makro 500 ml | KNO3 | 1.000 g |
| | | KCL | 7.450 g |
| | | MgSO4 7H2O | 3.200 g |
| | | KH2PO4 | 1.700 g |
| | | CaCl2 2H2O | 4.400 g |
| | | H2O topped to | 1000 ml |
| | BLG 29 mikro/MS 7 5 ml | UNDER STAM 10 ml | CuSO4 5H2O 0.025 g |
| | | | CoCl2 6H2O 0.025 g |
| | | | H2O 100 ml |
| | | H3BO3 | 0.62 g |
| | | MnSO4 H2O | 1.69 g |
| | | ZnSO4 7H2O | 0.86 g |
| | | KI | 0.083 g |
| | | Na2MoO4 2H2O | 0.025 g |
| | | H2O topped to | 100 ml |
| | FE EDTA 25.0 ml | FeSO4, 7H2O | 5.560 g |
| | | Na2EDTA, 2H2O | 7.450 g |
| | | Cas no 6381-92-6 | |
| | | H2O topped to | 1000 ml |
| | DCR-2 10.0 ml | Thiamine-HCl | 0.100 g |
| | | Pyridoxine HCl | 0.050 g |
| | | Nicotinic Acid | 0.050 g |
| | | Glycine | 0.200 g |
| | | H2O topped to | 100 ml |
| | Inositol 1.000 g | | |
| | H2O 2000 ml | | |
| ABA 30 ml | Abscisinsyre | 0.2640 g | |
| | Cas nr 14375-45-2 | | |
| | 0.1N NaHCO3 | 140 ml | |
| | H2O topped to | 2000 ml | |
| BLG amino 25 ml | L-glutamin | 29.000 g | |
| | L-asparagin | 2.000 g | |
| | Barnsteadwater | 800 ml | |
| | H20 topped to | 1000 ml | |
| PEG 4000 | 50 g | | |
| H20 topped to | 445 ml | | |
| Maltose | 45 g | | |
| H20 topped to | 500 ml | | |
| Phytagel | 1.8 g | | |

The cultures were grown at 20° C. in the dark for 3 weeks. Filter papers holding suitable cultures were moved to medium 29.75 grown at 20° C. in the dark for 3 weeks.

Medium 29.75: 1 Liter

| | |
|---|---|
| BLG - RAT | 200 ml |
| ABA | 40 ml* |
| PCIB | 25 ml |
| BLG-amino | 25 ml* |
| Maltose | 45 g** |
| Water topped to | 435 ml** |
| Water op to | 500 ml¤ |
| pH at 20-25° C. | 5.7 |
| Conductivity of Solution¤ | 2.39-2.65 mS |
| Phytagel | 1.8 g |

*Added after autoclaving

**PEG/the sugar, respectively, is mixed and autoclaved alone in the applied amount of water.

¤conductivity is measured in the solution of 500 ml, containing BLG-RAT and PCIB, after being set to pH 5.7

Recipes Used to Provide Medium 29.75

| | | | |
|---|---|---|---|
| BLG-Rat 200 ml | BLG 29 makro 500 ml | KNO3 | 1.000 g |
| | | KCL | 7.450 g |
| | | MgSO4 7H2O | 3.200 g |
| | | KH2PO4 | 1.700 g |
| | | CaCl2 2H2O | 4.400 g |
| | | H2O topped to | 1000 ml |
| | BLG 29 mikro/MS 7 5 ml | UNDER STAM 10 ml CuSO4 5H2O | 0.025 g |
| | | CoCl2 6H2O | 0.025 g |
| | | H2O topped to | 100 ml |
| | | H3BO3 | 0.62 g |
| | | MnSO4 H2O | 1.69 g |
| | | ZnSO4 7H2O | 0.86 g |
| | | KI | 0.083 g |
| | | Na2MoO4 2H2O | 0.025 g |
| | | H2O topped to | 100 ml |
| | FE EDTA 25.0 ml | FeSO4 7H2O | 5.560 g |
| | | Na2EDTA 2H2O | 7.450 g |
| | | Cas no 6381-92-6 | |
| | | H2O topped to | 1000 ml |
| | DCR-2 10.0 ml | Thiamine-HCl | 0.100 g |
| | | Pyridoxine HCl | 0.050 g |
| | | Nicotinic Acid | 0.050 g |
| | | Glycine | 0.200 g |
| | | H2O topped to | 100 ml |
| | Inositol 1.000 g | | |
| | H2O topped to 2000 ml | | |
| ABA 40 ml | | Abscisinsyre | 0.2640 g |
| | | Cas nr 14375-45-2 | |
| | | 0.1N NaHCO3 | 140 ml |
| | | H2O topped to | 2000 ml |
| PCIB 25 ml | | MCPA | 0.1070 g |
| | | Cas no 882-09-7 | |
| | | 0.1N KOH | 25.00 ml |
| | | H2O topped to | 500 ml |
| BLG amino 25 ml | | L-glutamin | 29.000 g |
| | | L-asparagin | 2.000 g |
| | | Barnsteadwater | 800 ml |
| | | H20 topped to | 1000 ml |
| Maltose | 45 g | | |
| H2O topped to | 435 ml | | |
| H20 topped to | 500 ml | | |
| Phytagel | 1.8 g | | |

Filter paper holding suitable cultures were then moved to medium 49.53 for 6 weeks for completing maturation of the embryos. Subsequently, the filter paper holding suitable embryos were removed to medium 8.95 for fattening and grown at 20° C. in the dark for two weeks in order to complete the maturation of the embryos.

Medium 8.95: 1 Liter

| | |
|---|---|
| KNV-8 RAT | 200 ml |
| BLG amino | 25 ml* |

-continued

| | |
|---|---|
| Sucrose | 75.0 g |
| Water topped to | 975 ml¤ |
| pH | 5.7 |
| Conductivity of solution¤ | 2.20-2.44 mS |
| Phytagel | 1.80 g |

*Added after autoclaving

¤ conductivity is measured in the solution of 975 ml, containing KNV-RAT and sucrose, after being set to pH 5.7

Recipes Used to Provide Medium 8.95:

| | | | | |
|---|---|---|---|---|
| KNV-Rat 200 ml | KNV-8 macro 2000 ml | Ca(NO3)2 4H2O | | 28.340 g |
| | | KNO3 | | 20.220 g |
| | | KH2PO4 | | 10.888 g |
| | | MgSO4 7H2O | | 19.720 g |
| | | NH4NO3 | | 14.400 g |
| | | KCL | | 5.964 g |
| | | H2O topped to | | 4.000 ml |
| | AXB- micro 20 ml | UNDER STAM 10 ml | | |
| | | | AlCl3, 6H2O | 0.024 g |
| | | | CoCl2, 6H2O | 0.012 g |
| | | | KI | 0.083 g |
| | | | NiCl2, 6H2O | 0.024 g |
| | | | H2O topped to | 100 ml |
| | | H3BO3 | 0.464 g | |
| | | CuSO4 5H2O | 0.025 g | |
| | | MnSO4 H2O | 0.423 g | |
| | | Na2MoO4 2H2O | 0.012 g | |

-continued

|  |  | ZnSO4 7H2O | 0.144 g |
|---|---|---|---|
|  |  | H2O topped to | 100 ml |
|  | FE EDTA 50 ml | FeSO4 7H2O | 5.560 g |
|  |  | Na2EDTA 2H2O | 7.450 g |
|  |  | Cas no 6381-92-0 |  |
|  |  | H2O topped to | 1000 ml |
|  | DCR-2 20 ml | Thiamine-HCl | 0.10 g |
|  |  | Pyridoxine HCl | 0.05 g |
|  |  | Nicotinic Acid | 0.05 g |
|  |  | Glycine | 0.20 g |
|  |  | H2O topped to | 100 ml |
|  | Inositol 2.00 g |  |  |
|  | H2O topped to 4000 ml |  |  |
| BLG amino 25 ml | L-glutamin | 29.000 g |  |
|  | L-asparagin | 2.000 g |  |
|  | Barnsteadwater | 800 ml |  |
|  | H20 topped to | 1000 ml |  |
| Sucrose | 75 g |  |  |
| H20 | 975 ml |  |  |
| Phytagel | 1.8 g |  |  |

The thus obtained fully mature cotyledonary somatic embryos (as shown in FIG. 1, number 7) were now ready for growing under conditions that stimulate the root formation.

Figure 2:
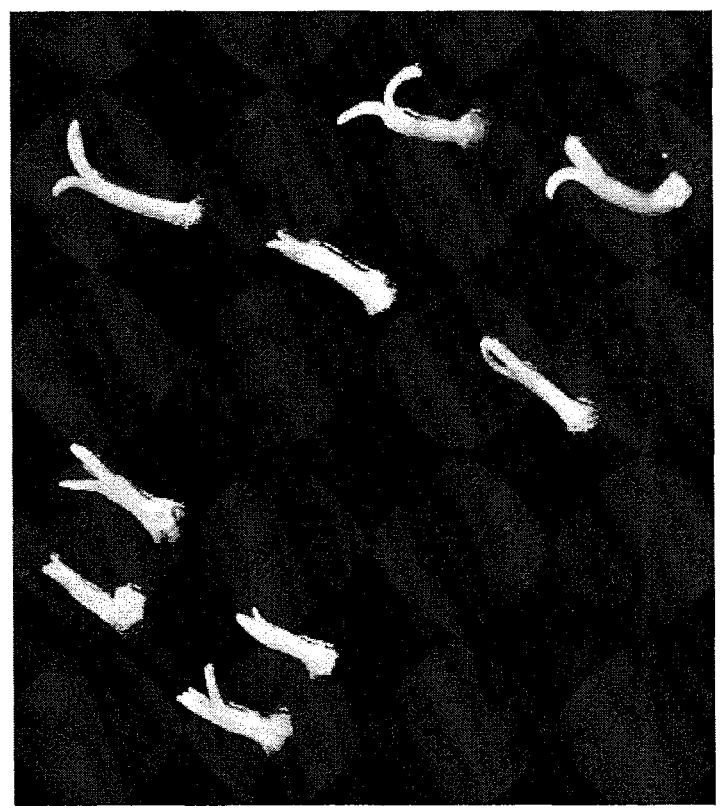
FIG. 2:
Fully mature cotyledonary embryos of SE *Abies nordmanniana*. These are in general 4-5 mm long, showing small cotyledons, typically 2-5 or more, and a radicle (root primordia), and a diameter at the center of the stem of 1 mm.

The fully mature somatic embryos selected for growing under root inducing conditions were characterized in being in general 4-5 mm long; having typically 2-5 or more small cotyledons; and a radicle (root primordia); and a diameter at the center of the stem of approximately 1 mm. Examples of fully mature embryos are shown in FIG. 2

Example 3: Rooting of Fully Mature Somatic Embryos of *Abies nordmanniana*

300 fully mature cotyledonary embryos (corresponding to stage 7 as shown in FIG. 1 and in FIG. 2) of each of the two *Abies nordmanniana* genotypes obtained from Example 2 were placed horizontally on rooting medium 51.21 in petri dishes comprising 20-40 embryos per dish. 60-80 embryos of each genotype were grown for 12-14 weeks in the dark at one of the following temperatures, respectively: 2° C., 4° C., 3-7° C., 9° C. and 10° C.

Medium 51.21: 1 Liter

| KNV Rat ml | 200.0 |
|---|---|
| Activated charcoal g | 10.000 |
| AgNO3 (250 mg/100 ml) ml | 1.00 |
| Sucrose g | 20.0 |
| Water up to ml | 1000¤ |
| Conductivity in solution¤ | 2.40-2.66 mS |
| pH | 5.7 |
| Agar g | 5.00 |

¤ conductivity is measured in the solution of 1000 ml, containing KNV-RAT, AgNO3 and sucrose, after being set to pH 5.7

Recipes Used to Provide the 51.21 Medium:

| KNV-Rat 200 ml | KNV-8 macro 2000 ml | Ca(NO3)2 4H2O | 28.340 g |
|---|---|---|---|
|  |  | KNO3 | 20.220 g |
|  |  | KH2PO4 | 10.888 g |
|  |  | MgSO4 7H2O | 19.720 g |
|  |  | NH4NO3 | 14.400 g |
|  |  | KCL | 5.964 g |
|  |  | H2O topped to | 4.000 ml |
|  | AXB- micro 20 ml | UNDER STAM 10 ml |  |
|  |  | AlCl3 6H2O | 0.024 g |
|  |  | CoCl2 6H2O | 0.012 g |
|  |  | KI | 0.083 g |
|  |  | NiCl2 6H2O | 0.024 g |
|  |  | H2O topped to | 100 ml |
|  |  | H3BO3 | 0.464 g |
|  |  | CuSO4 5H2O | 0.025 g |
|  |  | MnSO4 H2O | 0.423 g |
|  |  | Na2MoO4 2H2O | 0.012 g |
|  |  | ZnSO4 7H2O | 0.144 g |
|  |  | H2O topped to | 100 ml |
|  | FE EDTA 50 ml | FeSO4 7H2O | 5.560 g |
|  |  | Na2EDTA 2H2O | 7.450 g |
|  |  | Cas no 6381-92-6 |  |
|  |  | H2O topped to | 1000 ml |
|  | DCR-2 20 ml | Thiamine-HCl | 0.10 g |
|  |  | Pyridoxine HCl | 0.05 g |
|  |  | Nicotinic Acid | 0.05 g |
|  |  | Glycine | 0.20 g |
|  |  | H2O topped to | 100 ml |
|  | Inositol 2.00 g |  |  |
|  | H2O topped to 4000 ml |  |  |

| | |
|---|---|
| Activate charcoal | 10.000 g |
| AgNO3 (250 mg/100 ml) | 1.000 ml |
| Sucrose | 20.000 g |
| H2O topped to | 1000 ml |
| Agar | 5.000 g |

After 8, 9, 10, 11, 12 and 16 weeks, the embryos were checked for root formation and embryos with a well developed root were selected for further growth under the shoot inducing conditions described in Example 4.

Results:

Only a small share of the embryos of both genotypes that were grown at 2° C. or 9° C. developed a root after 8-16 weeks.

Very few of the embryos of both genotypes that were grown at 10° C. developed a root after 8-16 weeks.

The majority of the embryos of both genotypes that were grown at 4° C. or at 3-7° C. had developed a root after 12 weeks, a smaller number already after 8 weeks and a smaller number only after 16 weeks.

Figure 3:
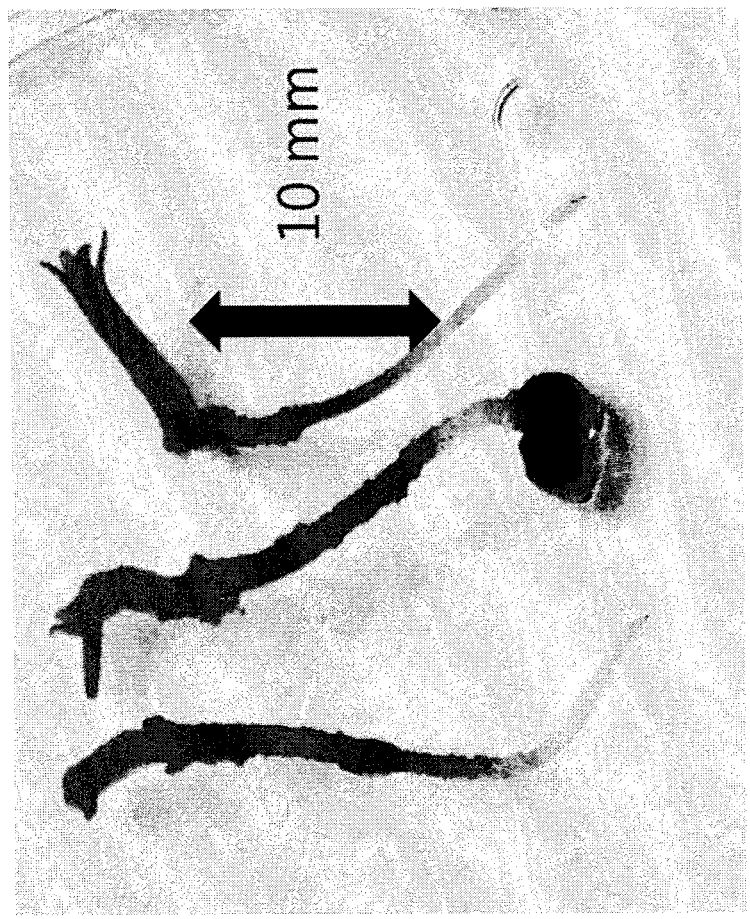
FIG. 3:
Small plantlets of SE *Abies nordmanniana* after growing under root inducing conditions of 3-7° C. for 8-14 weeks. The cotyledonary embryos/small plantlets have developed a root, the cotyledons are 1-5 mm long, and the hypocotyl is about 5-15 mm long.

Examples of suitable small plantlets that were chosen for further growth under shoot inducing conditions are shown in FIG. 3. These small plantlets were characterized in that the cotyledonary embryo had developed a root, the cotyledons were 1-5 mm long, and the hypocotyl was about 5-15 mm long.

Example 4: Shoot Development in Rooted Somatic Embryos of *Abies nordmanniana*

From each of the two *Abies nordmanniana* genotypes, 30-40 small plantlets that had developed a root when grown under each of the root inducing conditions described in Example 3 were selected for growing under shoot inducing conditions. Most of the selected small plantlets had been grown at 3-7° C. for 12-14 weeks as described in Example 3 since this was the temperature by which most of the somatic embryos successfully developed a root.

As mentioned in Example 3, small plantlets included in this experiment were characterized in having a root, the cotyledons were 1-5 mm long, and the hypocotyl was about 5-15 mm long.

The small plantlets were moved into plastic boxes (Eco2box, oval, Duchefa Bichemie) of 125 mm length×65 mm width×80 mm height having a lid. The lid was partially open for air-movement. The humidity RH % was kept above 90.

Each box contained 100 ml of the sugar-free medium 47.07.

Medium 47.07: 1 Liter

| | | |
|---|---|---|
| Duchefa WPM M0219 | 0.590 g | |
| DCR 2 | 0.250 ml | |
| AgNO3 (250 mg/100 ml) | 1.000 ml | |
| Inositol | 0.100 g | |
| Water topped to | 1000.0 ml¤ | |
| Conductivity of solution¤ | 751-830 μS | |
| pH | 5.7 | |
| Agar | 7.00 g | |
| Phytagel | 0.70 g | |

¤conductivity is measured in the solution of 1000 ml, containing WPM, DCR 2, AgNO3 and inositol, after being set to pH 5.7

Recipes Used to Provide Medium 47.07:

| | | | |
|---|---|---|---|
| Duchefa WPM M0219 | 0.590 g | | |
| DCR-2 | 250 ml | Thiamine-HCl | 0.100 g |
| | | Pyridoxine HCl | 0.050 g |
| | | Nicotinic Acid | 0.050 g |
| | | Glycine | 0.200 g |
| | | H2O topped to | 100 ml |
| AgNO3 (250 mg/100 ml) | 1 ml | | |
| Inositol | 0.1 g | | |
| Phytagel | 0.7 g | Gelrite, Duchefa Biochemie, CAS 71010-52-1 | |
| Italiensk Agar | 7 g | Plantager S1000, B&V Srl, Italy, CAS 9002-18-0 | |
| H2O topped to (pH = 5.7) | 1000 ml | | |

Each box comprised approximately 20-30 small plantlets of the same genotype, that had been grown under the same root inducing conditions.

The small plantlets were grown for 4 to 8 weeks at 15° in 24 h periods of white LED light of 70 to 400 μmol/m²s.

The light intensities were measured on top of each box as close to the cotyledons as possible, and thereafter accounting for the light reducing effect of the lit. The light intensities ranged from approximately 100 to 400 μmol/m²s depending on the distance from the nearest light source.

Figure 4:
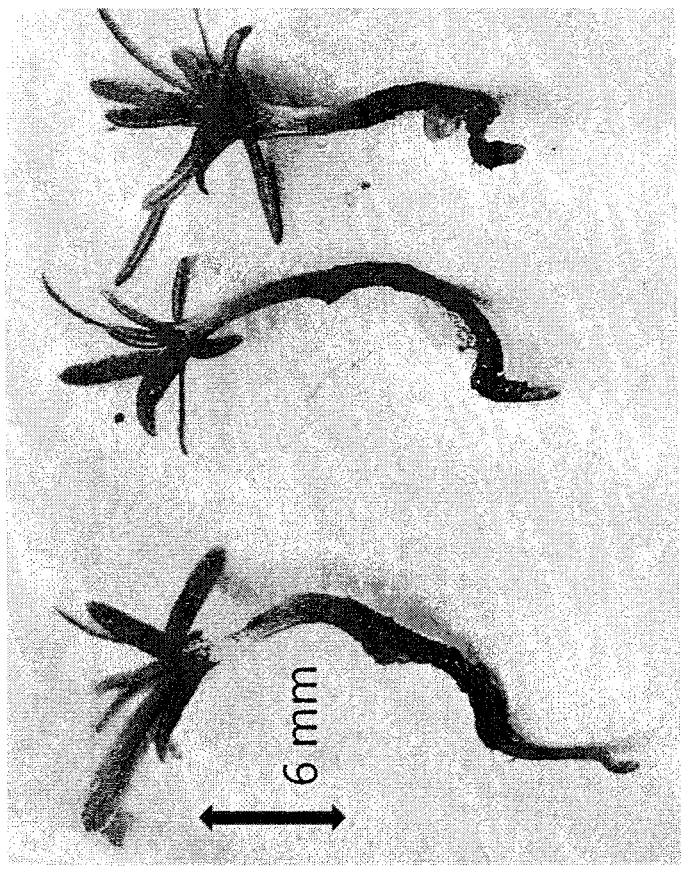
FIG. 4:
Emblings of SE *Abies nordmanniana* after growing under root inducing conditions of 3-7° C. for 8-14 weeks and subsequently under shoot inducing conditions in a sugar-free substrate at light intensities of 175-225 µmol/m²s by use of LED light at 15° C. for 4-6 weeks. The emblings are ready to be transplanted into small peat plugs

Results:

The majority of the small plantlets of both genotypes had developed into emblings having new cotyledons, which also had turned darker green showing a 'normal' surface of a fully developed conifer needle; after 6 weeks. The total height of these emblings above the root were generally 8-22 mm and the root was generally of a length in the range of 1-30 mm. Examples of such emblings are shown in FIG. 4.

A smaller amount of the plants of both genotypes had developed same characteristics after only 4-5 weeks, and a smaller amount of the plants of both genotypes had developed same after 7-8 weeks.

The majority of the plants of both genotypes that had developed new cotyledons, which also had turned darker green showing a 'normal' surface of a fully developed conifer needle after 4 to 8 weeks were plantlets that had been subjected to growth at 3-7° C. in the previous root inducing step

Example 5: Development of Small Plants of *Abies nordmanniana*

All well developed emblings with new cotyledons obtained from Example 4 were transferred to small forest C7 Jiffy pots of 025 mm plug for continued growth and were grown for 6-8 weeks at 25° C. in 24 h periods of white LED light of 100 to 400 μmol/m²s. The humidity RH % was slowly decreased to 70.

Almost all plants survived and were subsequently selected for continued nursery production.

Figure 5:
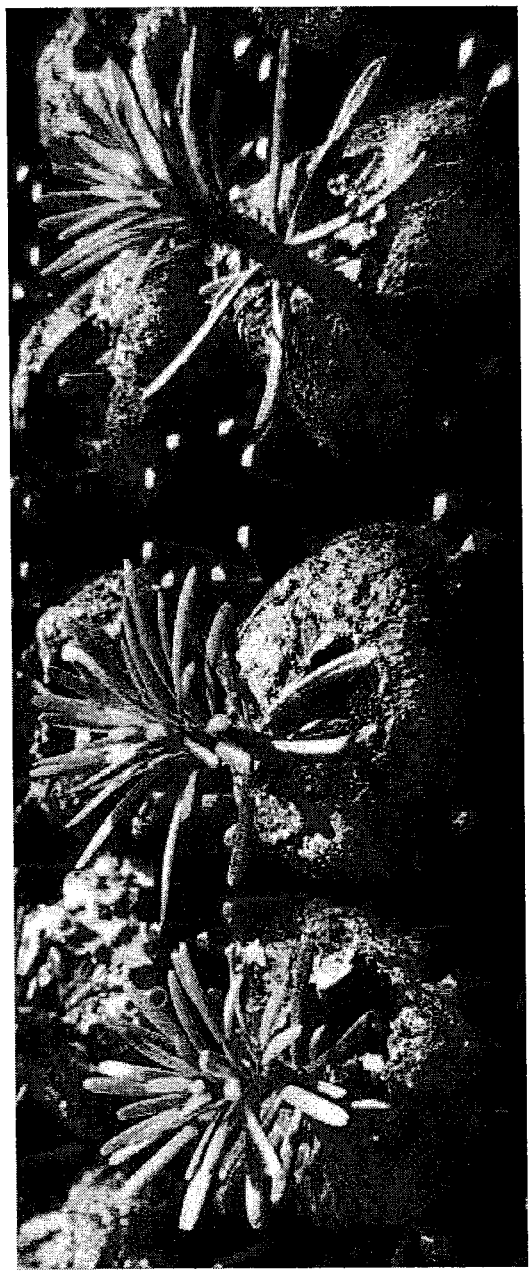
FIG. 5:
Well developed emblings of SE *Abies nordmanniana* in small pots of ø25 mm plug after having grown under root inducing conditions of 3-7° C. for 8-14 weeks and subsequently under shoot inducing conditions in a sugar-free substrate at light intensities of 175-225 µmol/m²s by use of LED light at 15° C. for 4-6 weeks followed by growth for 6-8 weeks at 25° C. in 24 h periods of white LED light of 100 to 400 µmol/m²s.

Examples of emblings growing into small plants at this stage are shown in FIG. 5.

Example 6: Nursery Production of Small Plants of *Abies nordmanniana*

Plants obtained from Example 5 were potted into larger pots and grown in a greenhouse for 1-2 years until a suitable size for growing outside (for instance in a field for Christmas tree production) was reached.

Figure 6:
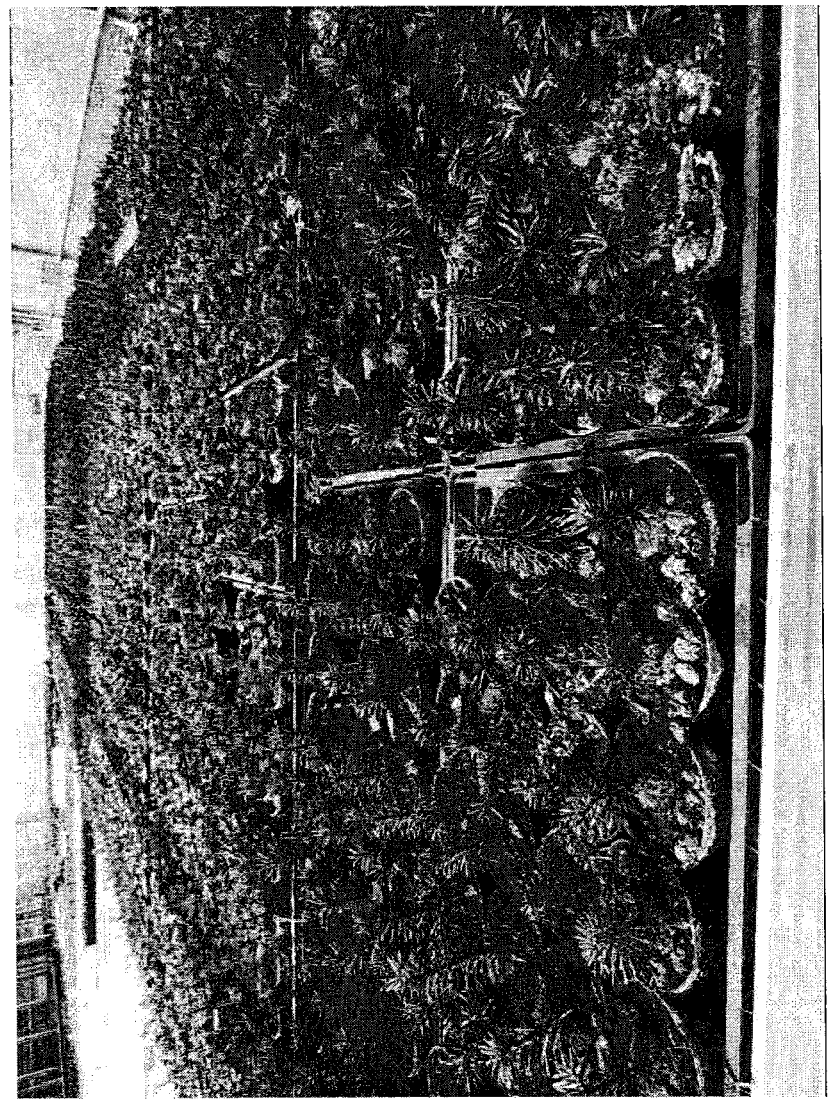
FIG. 6:
Small plants of SE *Abies nordmanniana* growing in a nursery. The plants have been grown under root inducing conditions of 3-7° C. for 8-14 weeks and subsequently under shoot inducing conditions in a sugar-free substrate at light intensities of 175-225 µmol/m²s by use of LED light at 15° C. for 4-6 weeks followed by growth for 6-8 weeks at 25° C. in 24 h periods of white LED light of 100 to 400 µmol/m²s, followed by 1-2 years of growing in a greenhouse. The plants still need one more growing season before being planted outside for instance in a field for Christmas tree production.

Examples of commercial emblings of *Abies nordmanniana* obtained from conditions described in Example 5 and the previous Examples are shown in FIG. 6. The plants in FIG. 6 still need one season more before planting out.

Example 7: Preparation of Somatic Embryos of *Abies bornmülleriana*

Cones of *Abies bornmülleriana* was collected from the Danish seed orchard FP.267 Kongsøre, north of Holbæk. Seed trees were selected in a Danish Christmas tree stand originating from the area near Bolu Kökez in Turkey. The cones were cleaned and rinsed in water and disinfected with fungicide and ethanol. The cones were then stored at 5° C. for up to 60 days.

The seeds were then isolated from the cone by breaking the cone into pieces and collecting the seeds. The seeds were placed in a 35% hydrogen peroxide solution diluted 1:10 for 3-5 minutes while stirring. The seeds were then removed to a mild Presept® solution (1 tablet comprising troclosene sodium in 1 liter of water and two drops of detergent (Tween)) for 24 hours while ensuring access to oxygen to the solution by stirring. The seeds were then wrapped in gaze briefly for drying and subsequently rinsed in 70% ethanol for 3 minutes. This will also separate vital seeds from dead seeds; the vital seeds will sink whereas the dead seeds flow. Only the vital seeds were collected for further processing. The vital seeds were removed to a Precept solution (1 tablet in 0.5 L sterile water and 3-4 drops of detergent (Tween)) and placed on a shaker for 10 minutes. The seeds were then rinsed 3 times in sterile water under sterile conditions. If seeds have been stored for a long time or if they appear unclean, the can be briefly immersed into 96% ethanol and flamed.

The cleaned seeds where cut open and the seed embryo removed. Each embryo was placed in a petri dish comprising growth medium 29.4 in order to initiate the somatic cell culture. The cultures were grown at 20° C. in the dark for 10 to 16 weeks.

Medium 29.4: 1 Liter

| | |
|---|---|
| H2O | 200 ml |
| BLG - RAT | 200 ml |
| BAP | 5.0 ml |
| BLG amino | 25 ml * |
| Sucrose | 10 g |
| Water up to | 975 ml¤ |
| Conductivity of solution¤ | 1.241-1.371 mS |
| pH | 5.7 |
| Phytagel | 1.8 g |

* Added after autoclaving

¤: conductivity is measured in the solution of 975 ml, containing BLG-RAT, BAP and sucrose, after being set to pH 5.7.

Recipes Used to Provide Medium 29.4:

| | | | | |
|---|---|---|---|---|
| BLG-Rat 200 ml | BLG 29 makro 500 ml | KNO3 | 1.000 g | |
| | | KCL | 7.450 g | |
| | | MgSO4 7H2O | 3.200 g | |
| | | KH2PO4 | 1.700 g | |
| | | CaCl2 2H2O | 4.400 g | |
| | | H2O topped to | 1000 ml | |
| | BLG 29 mikro/MS 7 5 ml | UNDER STAM 10 ml | CuSO4 5H2O | 0.025 g |
| | | | CoCl2 6H2O | 0.025 g |
| | | | H2O topped to | 100 ml |
| | | H3BO3 | 0.62 g | |
| | | MnSO4 H2O | 1.69 g | |
| | | ZnSO4 7H2O | 0.86 g | |
| | | KI | 0.083 g | |
| | | Na2MoO4 2H2O | 0.025 g | |
| | | H2O topped to | 100 ml | |
| | FE EDTA 25.0 ml | FeSO4, 7H2O | 5.560 | |
| | | Na2EDTA, 2H2O | 7.450 g | |
| | | Cas no 6381-92-6 | | |
| | | H2O topped to | 1000 ml | |
| | DCR-2 10.0 ml | Thiamine-HCl | 0.100 g | |
| | | Pyridoxine HCl | 0.050 g | |
| | | Nicotinic Acid | 0.050 g | |
| | | Glycine | 0.200 g | |
| | | H2O topped to | 100 ml | |
| | Inositol 1.000 g | | | |
| | H2O topped to 2000 ml | | | |
| BAP 5 ml | | BAP | 0.0225 g | |
| | | Cas no 1214-39-7 | | |
| | | 1.0N KOH | 1.4 ml | |
| | | H2O topped to | 100 ml | |
| BLG amino 25 ml | | L-glutamin | 29.000 g | |
| | | L-asparagin | 2.000 g | |
| | | Barnsteadwater | 800 ml | |
| | | H20 topped to | 1000 ml | |
| Sucrose | | 10 g | | |
| H20 | | 975 ml | | |
| Phytagel | | 1.8 g | | |

Samples of the somatic cell culture can optionally be prepared for cryopreservation or be used directly for embryo development and maturation.

If the samples were cryopreserved, approximately 2 gram of tissue from one specific genotype were placed in a sterile bottle and 20 g of medium 29.4 was added, and 1 ml Sorbitol. The cultures were placed on a shaker providing constant agitation for adequate aeration for 24 hours at 20° C. and 1 ml sorbitol was added. After 48 hours samples were placed at 0° C. for at least 30 min. Then, 1 ml DMSO was added to each bottle. The solution were divided into 12 tubes and slowly frozen from 0.5° C. to −35° C. before being transferred to a cryo-tank at minus 180° C.

When applicable, the somatic cell cultures were thawed and the development of somatic embryos was initiated.

The samples were thawed in 40° C. water, disinfected in ethanol and poured onto filter paper in a petri dish. After 1 hour the cultures were removed to a clean filter paper, and again after 18 hours the cultures were placed in a new petri dish comprising a growth medium, such as medium 29.4.

The cultures are grown at 20° C. and the viability of the cultures are checked every $2^{nd}$ week. After 6 weeks, viable cultures are selected for embryo development and maturation. Every 2nd week cultures were moved onto fresh medium 29.4. After another 6-8 weeks the cultures were ready.

Example 8: Embryo Development and Maturation of *Abies bornmülleriana*

Somatic cell cultures from two different genotypes of *Abies bornmülleriana* obtained from example 7 were selected for embryo development and maturation.

For each sample of somatic cell culture, 4 g of culture were added to 100 g 29.4 medium and blended for 25 seconds. The samples were then left for 30 minutes and any surplus liquid was removed until 30 ml. One ml of the blend was pipetted onto filter paper in a petri dish comprising 15 ml 49.53 medium.

Medium 49.53: 1 Liter

| | |
|---|---|
| BLG - RAT | 200 ml |
| ABA | 30 ml* |
| BLG-Amino | 25 ml* |
| PEG-4000 | 50 g** |
| Maltose | 45 g** |
| Water topped to | 445 ml** |
| Water up to | 500 ml¤ |
| pH | 5.7 |
| Conductivity of solution¤ | 2.39-2.65 mS |
| Phytagel | 1.8 g |

*Added after autoclaving

**PEG/the sugar, respectively, is mixed and autoclaved alone in the applied amount of water. The RAT-media can be obtained from common distributors such as Duchefa Biochemie.

¤: conductivity is measured in the solution of 500 ml, containing BLG-RAT, after being set to pH 5.7

Recipes Used to Provide Medium 49.53

| | | | | |
|---|---|---|---|---|
| BLG-Rat 200 ml | BLG 29 makro 500 ml | KNO3 | 1.000 g | |
| | | KCL | 7.450 g | |
| | | MgSO4 7H2O | 3.200 g | |
| | | KH2PO4 | 1.700 g | |
| | | CaCl2 2H2O | 4.400 g | |
| | | H2O topped to | 1000 ml | |
| | BLG 29 mikro/MS 7 5 ml | UNDER STAM 10 ml | CuSO4 5H2O | 0.025 g |
| | | | CoCl2 6H2O | 0.025 g |
| | | | H2O | 100 ml |
| | | H3BO3 | 0.62 g | |
| | | MnSO4 H2O | 1.69 g | |
| | | ZnSO4 7H2O | 0.86 g | |
| | | KI | 0.083 g | |
| | | Na2MoO4 2H2O | 0.025 g | |
| | | H2O topped to | 100 ml | |
| | FE EDTA 25.0 ml | FeSO4, 7H2O | 5.560 g | |
| | | Na2EDTA, 2H2O | 7.450 g | |
| | | Cas no 6381-92-6 | | |
| | | H2O topped to | 1000 ml | |
| | DCR-2 10.0 ml | Thiamine-HCl | 0.100 g | |
| | | Pyridoxine HCl | 0.050 g | |
| | | Nicotinic Acid | 0.050 g | |
| | | Glycine | 0.200 g | |
| | | H2O topped to | 100 ml | |
| | Inositol 1.000 g | | | |
| | H2O 2000 ml | | | |
| ABA 30 ml | Abscisinsyre | 0.2640 g | | |
| | Cas nr 14375-45-2 | | | |
| | 0.1N NaHCO3 | 140 ml | | |
| | H2O topped to | 2000 ml | | |
| BLG amino 25 ml | L-glutamin | 29.000 g | | |
| | L-asparagin | 2.000 g | | |
| | Barnsteadwater | 800 ml | | |
| | H20 topped to | 1000 ml | | |
| PEG 4000 | 50 g | | | |
| H20 topped to | 445 ml | | | |
| Maltose | 45 g | | | |
| H20 topped to | 500 ml | | | |
| Phytagel | 1.8 g | | | |

The cultures were grown at 20° C. in the dark for 3 weeks. Filter papers holding suitable cultures were moved to medium 29.75 grown at 20° C. in the dark for 3 weeks.

Medium 29.75: 1 Liter

| | |
|---|---|
| BLG - RAT | 200 ml |
| ABA | 40 ml* |
| PCIB | 25 ml |
| BLG - amino | 25 ml* |
| Maltose | 45 g** |
| Water topped to | 435 ml** |
| Water op to | 500 Ml¤ |
| pH at 20-25° C. | 5.7 |
| Conductivity of Solution¤ | 2.39-2.65 mS |
| Phytagel | 1.8 g |

*Added after autoclaving
**PEG/the sugar, respectively, is mixed and autoclaved alone in the applied amount of water.
¤: conductivity is measured in the solution of 500 ml, containing BLG-RAT and PCIB, after being set to pH 5.7

Recipes Used to Provide Medium 29.75

| | | | | |
|---|---|---|---|---|
| BLG-Rat 200 ml | BLG 29 makro 500 ml | KNO3 | 1.000 g | |
| | | KCL | 7.450 g | |
| | | MgSO4 7H2O | 3.200 g | |
| | | KH2PO4 | 1.700 g | |
| | | CaCl2 2H2O | 4.400 g | |
| | | H2O topped to | 1000 ml | |
| | BLG 29 mikro/MS 7 5 ml | UNDER STAM 10 ml | CuSO4 5H2O | 0.025 g |
| | | | CoCl2 6H2O | 0.025 g |
| | | | H2O topped to | 100 ml |
| | | H3BO3 | 0.62 g | |
| | | MnSO4 H2O | 1.69 g | |
| | | ZnSO4 7H2O | 0.86 g | |
| | | KI | 0.083 g | |
| | | Na2MoO4 2H2O | 0.025 g | |
| | | H2O topped to | 100 ml | |
| | FE EDTA 25.0 ml | FeSO4 7H2O | 5.560 g | |
| | | Na2EDTA 2H2O | 7.450 g | |
| | | Cas no 6381-92-6 | | |
| | | H2O topped to | 1000 ml | |
| | DCR-2 10.0 ml | Thiamine-HCl | 0.100 g | |
| | | Pyridoxine HCl | 0.050 g | |
| | | Nicotinic Acid | 0.050 g | |
| | | Glycine | 0.200 g | |
| | | H2O topped to | 100 ml | |
| | Inositol 1.000 g | | | |
| | H2O topped to 2000 ml | | | |
| ABA 40 ml | Abscisinsyre | 0.2640 g | | |
| | Cas nr 14375-45-2 | | | |
| | 0.1N NaHCO3 | 140 ml | | |
| | H2O topped to | 2000 ml | | |
| PCIB 25 ml | MCPA | 0.1070 g | | |
| | Cas no 882-09-7 | | | |
| | 0.1N KOH | 25.00 ml | | |
| | H2O topped to | 500 ml | | |
| BLG amino 25 ml | L-glutamin | 29.000 g | | |
| | L-asparagin | 2.000 g | | |
| | Barnsteadwater | 800 ml | | |
| | H20 topped to | 1000 ml | | |
| Maltose | 45 g | | | |
| H2O topped to | 435 ml | | | |
| H20 topped to | 500 ml | | | |
| Phytagel | 1.8 g | | | |

Filter paper holding suitable cultures were then moved to medium 49.53 for 6 weeks for completing maturation of the embryos. Subsequently, the filter paper holding suitable embryos were removed to medium 8.95 for fattening and grown at 20° C. in the dark for two weeks in order to complete the maturation of the embryos.

Medium 8.95: 1 Liter

| | |
|---|---|
| KNV-8 RAT | 200 ml |
| BLG amino | 25 ml* |
| Sucrose | 75.0 g |
| Water topped to | 975 ml¤ |
| pH | 5.7 |
| Conductivity of solution¤ | 2.20-2.44 mS |
| Phytagel | 1.80 g |

*Added after autoclaving
¤: conductivity is measured in the solution of 975 ml, containing KNV-RAT and sucrose, afer being set to pH 5.7

Recipes Used to Provide Medium 8.95:

| | | | | |
|---|---|---|---|---|
| KNV-Rat 200 ml | KNV-8 macro 2000 ml | Ca(NO3)2 4H2O | 28.340 | g |
| | | KNO3 | 20.220 | g |
| | | KH2PO4 | 10.888 | g |
| | | MgSO4 7H2O | 19.720 | g |
| | | NH4NO3 | 14.400 | g |
| | | KCL | 5.964 | g |
| | | H2O topped to | 4.000 | ml |
| | AXB- micro 20 ml | UNDER STAM 10 ml | | |
| | | AlCl3, 6H2O | 0.024 | g |
| | | CoCl2, 6H2O | 0.012 | g |
| | | KI | 0.083 | g |
| | | NiCl2, 6H2O | 0.024 | g |
| | | H2O topped to | 100 | ml |
| | | H3BO3 | 0.464 | g |
| | | CuSO4 5H2O | 0.025 | g |
| | | MnSO4 H2O | 0.423 | g |
| | | Na2MoO4 2H2O | 0.012 | g |
| | | ZnSO4 7H2O | 0.144 | g |
| | | H2O topped to | 100 | ml |
| | FE EDTA 50 ml | FeSO4 7H2O | 5.560 | g |
| | | Na2EDTA 2H2O | 7.450 | g |
| | | Cas no 6381-92-6 | | |
| | | H2O topped to | 1000 | ml |
| | DCR-2 20 ml | Thiamine-HCl | 0.10 | g |
| | | Pyridoxine HCl | 0.05 | g |
| | | Nicotinic Acid | 0.05 | g |
| | | Glycine | 0.20 | g |
| | | H2O topped to | 100 | ml |
| | Inositol 2.00 g | | | |
| | H2O topped to 4000 ml | | | |
| BLG amino 25 ml | L-glutamin | 29.000 | g | |
| | L-asparagin | 2.000 | g | |
| | Barnsteadwater | 800 | ml | |
| | H20 topped to | 1000 | ml | |
| Sucrose | 75 g | | | |
| H20 | 975 ml | | | |
| Phytagel | 1.8 g | | | |

The thus obtained fully mature cotyledonary somatic embryos (as shown in FIG. 1, number 7) were now ready for growing under conditions that stimulate the root formation.

The fully mature somatic embryos selected for growing under root inducing conditions were characterized in being in general 4-5 mm long; having typically 2-5 or more small cotyledons; and a radicle (root primordia); and a diameter at the center of the stem of approximately 1 mm

Example 9: Rooting of Fully Mature Somatic Embryos of *Abies bornmülleriana*

Approximately 300 fully mature cotyledonary embryos (corresponding to stage 7 as shown in FIG. 1) of each of the two *Abies bornmülleriana* genotypes obtained from Example 8 are placed horizontally on rooting medium 51.21 in petri dishes comprising 30-40 embryos per dish. 60-80 embryos of each genotype are grown for 12-14 weeks in the dark at one of the following temperatures, respectively: 2° C., 4° C., 3-7° C., 9° C. and 10° C.

After 8, 9, 10, 11, 12 and 16 weeks, the embryos are checked for root formation and embryos with a well developed root are selected for further growth under the shoot inducing conditions described in Example 10.

Medium 51.21: 1 Liter

| | |
|---|---|
| KNV Rat ml | 200.0 |
| Activated charcoal g | 10.000 |
| AgNO3 (250 mg/100 ml) ml | 1.00 |
| Sucrose g | 20.0 |
| Water up to ml | 1000 ¤ |
| Conductivity in solution ¤ | 2.40-2.66 mS |
| pH | 5.7 |
| Agar g | 5.00 |

¤: conductivity is measured in the solution of 1000 ml, containing KNV-RAT, AgNO3 and sucrose, after being set to pH 5.7

Recipes Used to Provide the 51.21 Medium:

| | | | | |
|---|---|---|---|---|
| KNV-Rat 200 ml | KNV-8 macro 2000 ml | Ca(NO3)2 4H2O | 28.340 | g |
| | | KNO3 | 20.220 | g |
| | | KH2PO4 | 10.888 | g |
| | | MgSO4 7H2O | 19.720 | g |
| | | NH4NO3 | 14.400 | g |
| | | KCL | 5.964 | g |
| | | H2O topped to | 4.000 | ml |
| | AXB- micro 20 ml | UNDER STAM 10 ml | | |
| | | AlCl3 6H2O | 0.024 | g |
| | | CoCl2 6H2O | 0.012 | g |
| | | KI | 0.083 | g |

-continued

|  |  |  |  |
|---|---|---|---|
|  |  | NiCl2 6H2O | 0.024 g |
|  |  | H2O topped to | 100 ml |
|  | H3BO3 | 0.464 g |  |
|  | CuSO4 5H2O | 0.025 g |  |
|  | MnSO4 H2O | 0.423 g |  |
|  | Na2MoO4 2H2O | 0.012 g |  |
|  | ZnSO4 7H2O | 0.144 g |  |
|  | H2O topped to | 100 ml |  |
| FE EDTA 50 ml | FeSO4 7H2O | 5.560 g |  |
|  | Na2EDTA 2H2O Cas no 6381-92-6 | 7.450 g |  |
|  | H2O topped to | 1000 ml |  |
| DCR-2 20 ml | Thiamine-HCl | 0.10 g |  |
|  | Pyridoxine HCl | 0.05 g |  |
|  | Nicotinic Acid | 0.05 g |  |
|  | Glycine | 0.20 g |  |
|  | H2O topped to | 100 ml |  |
| Inositol 2.00 g |  |  |  |
| H2O topped to 4000 ml |  |  |  |
| Activate charcoal | 10.000 g |  |  |
| AgNO3 (250 mg/100 ml) | 1.000 ml |  |  |
| Sucrose | 20.000 g |  |  |
| H20 topped to | 1000 ml |  |  |
| Agar | 5.000 g |  |  |

Results:

Only a small share of the embryos of both genotypes that are grown at 2° C. or 9° C. will have developed a root after 8-16 weeks.

Very few of the embryos of both genotypes that are grown at 10° C. will have developed a root after 8-16 weeks.

The majority of the embryos of both genotypes that are grown at 4° C. or at 3-7° C. will have developed a root after 12 weeks, a smaller number already after 8 weeks and a smaller number only after 16 weeks.

These small plantlets thus obtained that are suitable for further growth under the shoot inducing conditions are characterized in that the cotyledonary embryo has developed a radicle (root), the cotyledons are 1-5 mm long and green, and the hypocotyl is about 10-20 mm long.

Example 10: Shoot Development of Small Plantlets of *Abies bornmülleriana*

From each of the two *Abies bornmülleriana* genotypes, 30-40 small plantlets that will have developed a root when grown under each of the root inducing conditions described in Example 3 are selected for growing under shoot inducing conditions. Most of the selected plantlets will be plants that have grown at a cold period of 3-7° C. as described in Example 9 since this will be the temperature by which most of the somatic embryos successfully develops a root.

As mentioned in Example 3, the small plantlets included in this experiment are characterized in having a root, the cotyledons are 1-5 mm long and green, and the hypocotyl is about 5-15 mm long.

The small plantlets are moved into plastic boxes (Eco2box, oval, Duchefa Bichemie) of 125 mm length×65 mm width×80 mm height having a lid. The lid was partially open for air-movement. The humidity RH % was kept above 90.

Each box contained 100 ml of the sugar-free medium 47.07.

Medium 47.07: 1 Liter

| Duchefa WPM M0219 | 0.590 g |
|---|---|
| DCR 2 | 0.250 ml |
| AgNO3 (250 mg/100 ml) | 1.000 ml |
| Inositol | 0.100 g |
| Water topped to | 1000.0 ml ¤ |
| Conductivity of solution ¤ | 751-830 μS |
| pH | 5.7 |
| Agar | 7.00 g |
| Phytagel | 0.70 g |

¤ : conductivity is measured in the solution of 1000 ml, containing WPM, DCR 2, AgNO3 and inositol, after being set to pH 5.7

Recipes Used to Provide Medium 47.07:

| Duchefa WPM M0219 | 0.590 g |  |  |  |
|---|---|---|---|---|
| DCR-2 | 250 ml | Thiamine-HCl | 0.100 | g |
|  |  | Pyridoxine HCl | 0.050 | g |
|  |  | Nicotinic Acid | 0.050 | g |
|  |  | Glycine | 0.200 | g |
|  |  | H2O topped to | 100 | ml |
| AgNO3 (250 mg/100 ml) | 1 ml |  |  |  |
| Inositol | 0.1 g |  |  |  |
| Phytagel | 0.7 g | Gelrite, Duchefa Biochemie, CAS 71010-52-1 |  |  |
| Italiensk Agar | 7 g | Plantager S1000, B&V Srl, Italy, CAS 9002-18-0 |  |  |
| H2O topped to (pH = 5.7) | 1000 ml |  |  |  |

Each box comprises approximately 24-30 small plantlets of the same genotype that will have been grown under the same root inducing conditions.

The small plantlets are grown for 4 to 8 weeks at 15° in 24 h periods of white LED light of 70 to 400 μmol/m²s.

The light intensities are measured inside each box as close to the cotyledons as possible. The light intensities ranges from approximately 100 to 400 μmol/m²s depending on the distance from the nearest light source.

Results:

The majority of the small plantlets of both genotypes will have developed new cotyledons, which also have turned darker green showing a 'normal' surface of a fully developed conifer needle after 6 weeks. The total height of these emblings above the root are generally 8-22 mm and the root is generally of a length in the range of 1-30 mm.

A smaller amount of the emblings of both genotypes will have developed same characteristics after only 4-5 weeks, and a smaller amount of the plants of both genotypes will have developed same after 7-8 weeks.

The majority of the emblings of both genotypes that will have developed new cotyledons, which also have turned darker green showing a 'normal' surface of a fully developed conifer needle after 4 to 8 weeks will be plantlets that have been grown at 3-7° C. in the previous root inducing step

Example 11: Development of Small Plants of *Abies bornmülleriana*

All well developed emblings with new cotyledons obtained from Example 10 will be transferred to small forest C7 Jiffy pots of ø25 mm plug for continued growth and will be grown for 6-8 weeks at 25° C. in 24 h periods of white LED light of 100 to 400 µmol/m²s. The humidity RH % will slowly be decreased to 70.

Almost all plants will have survived and will subsequently be selected for continued nursery production.

Example 12: Comparison of Developmental Stage of Somatic Embryos or Small Plantlets Grown without any Root Inducing Conditions A number of mature somatic embryos of two different genotypes of *Abies nordmanniana* obtained from Example 2 and two different genotypes of *Abies bornmülleriana* obtained from Example 8 is grown at the shoot inducing conditions described in Example 4 and in Example 10, respectively, i.e. without previous growth under the root inducing conditions described in Example 3 and in Example 11, respectively.

For all 4 genotypes, the survival rate of the plantlets will be significantly lower compared to genotypes of the same kind, that are to be grown under both the root inducing conditions described in Example 3 and in Example 9, respectively, and under the shoot inducing conditions described in Example 4 and in Example 10, respectively.

Example 13: Comparison of Developmental Stage of Small Plantlets Grown without any Shoot Inducing Conditions A number of small rooted plantlets of two different genotypes of *Abies nordmanniana* and of *Abies bornmülleriana*, respectively, obtained from Example 3 and from Example 9, respectively, will be grown into small plantlets under the conditions described in Example 5 and in Example 11, respectively, i.e. without previous growth under the shoot inducing conditions described in Example 4 and in Example 10, respectively.

For all 4 genotypes, the survival rate of the plantlets will be significantly lower compared to genotypes of the same kind, that are to be grown under both the root inducing conditions described in Example 3 and in Example 9, respectively, and under the shoot inducing conditions described in Example 4 and in Example 10, respectively.

Example 14: Features Influencing the Survival Rate

The impact of growing small plantlets in air-tight boxes vs. growing these in boxes wherein part of the lid had been removed was tested in order to find out whether this had any influence on the development and survival rate of the small plantlets. Further, different media were tested.

The test was performed on 240 rooted embryos/small plantlets of *Abies nordmanniana* of two different genotypes that had been provided, developed and subsequently grown as described in Examples 1 to 3, respectively, where the conditions described in Example 3 were selected to growth of 3-7° C. for 12 weeks.

The small plantlets had thus all developed a root, cotyledons of 1-5 mm long and green, and a hypocotyl of about 5-15 mm. At this developmental stage, the small plantlets were separated into two groups of 120 plants—one group for growing in air-tight boxes and the other group for growing in boxes where continuous access to air was secured by removing approximately 20% of the lid.

Each group of 120 rooted embryos were divided into four groups of 30 plants each and grown in a box containing one of the following four media:

47.037: Double strength of media 47.07 as described in Examples 4 and 10, respectively 47.06: Double strength of media 47.07 as described in Examples 4 and 10, respectively with the addition of 3 types of auxins and Cu 47.07: This media is described in Examples 4 and 10, respectively 47.08: Media 47.07 as described in Examples 4 and 10, respectively with the addition of 3 types of auxins and Cu The plants were then grown in the same chamber for 6 weeks at 15° in 24 h periods of white LED light of 100 to 400 µmol/m²s.

After the 6 weeks, the survival rate was determined and on the survived plantlets, the percentage of the plantlets having developed a green top, a bud and having a white root was determined. In some of the survived plantlets the root had turned black. A black root indicates that the plantlets will have less chance of surviving when transferred into a plug or soil.

Results:

As evident from the below table, the a significantly higher percentage of the small plantlets that were grown in boxes where part of the lid was open to air survived compared to the small plantlets that were grown in air-tight boxes with the same media. The access to air did, however, not appear to influence the percentages of the survived plantlets having a green top, a bud or a white root.

| Media | % living | % green top | % with bud | % white root |
|---|---|---|---|---|
| 47.037 | 51 | 95 | 72 | 16 |
| 47.06 | 18 | 78 | 22 | 12 |
| 47.07 | 56 | 100 | 73 | 8 |
| 47.08 | 26 | 49 | 13 | 0 |
| 47.037 + air | 77 | 97 | 68 | 12 |
| 47.06 + air | 33 | 55 | 24 | 3 |
| 47.07 + air | 77 | 93 | 75 | 6 |
| 47.08 + air | 35 | 54 | 12 | 0 |

It can thus be concluded, that it is beneficial for the survival rates that plants grown under the shoot inducing growth conditions according to the method of the present invention are grown under circumstances where access to air is secured.

It is also evident from the results that the media wherein the rooted embryos are grown greatly influences both the percentage of the small plantlets that survive, and also the percentage of plantlets having a green top, a bud and a white root.

Thus, finding the optimum media for a specific species may require some routine optimization tests.

Example 15: Impact of Temperature at the Shoot Inducing Step 8 boxes wherein the lid was partially open comprising approximately 30 small plantlets of *Abies nordmanniana* of different genotypes was obtained from a process comprising the steps as described in Examples 1, 2 and 3, wherein the cold treatment period in the root inducing step was 3-7° C. for 12 weeks were grown at different temperatures in order to find the more beneficial temperature for inducing top shoot formation while at the same time stimulating further root development.

The boxes were placed at one of the following 8 temperatures for 4 weeks in 24 h light periods from LED at light intensities from 100-300 µmol/m²s and subsequently, the percentages of the small plantlets having developed into emblings having shoots and further rooting was evaluated.

Figure 7:
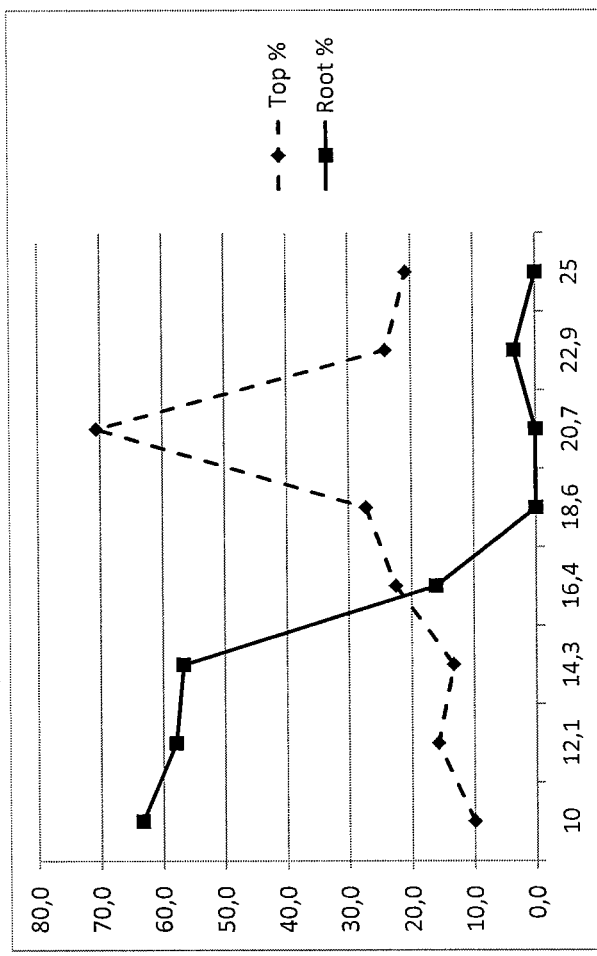
FIG. 7:
Diagram showing the impact of the temperature (x-axis) on the percentage of plants (y-axis) having developed of a top (shoot) and continued root development, respectively. The plants are SE *Abies nordmanniana* after growing under root inducing conditions of 3-7° C. for 8-14 weeks and subsequent under shoot inducing conditions in a sugar-free substrate at light intensities of 175-225 µmol/m²s by use of LED light at temperatures of 10° C., 12.1° C., 14.3° C., 16.4° C., 18.6° C., 20.7° C., 22.9° C. or 25° C., respectively, for 4-6 weeks.

The results are shown in the below table and in FIG. 7:

| Temperature | Box no. | No. of plants | No. having developed top shoot | % having developed top shoot | No. having developed white roots | % having developed white roots |
|---|---|---|---|---|---|---|
| 10 | 1 | 30 | 3 | 10.0 | 19 | 63.3 |
| 12.1 | 2 | 38 | 6 | 15.8 | 22 | 57.9 |
| 14.3 | 3 | 30 | 4 | 13.3 | 17 | 56.7 |
| 16.4 | 4 | 31 | 7 | 22.6 | 5 | 16.1 |
| 18.6 | 5 | 33 | 9 | 27.3 | 0 | 0.0 |
| 20.7 | 6 | 17 | 12 | 70.6 | 0 | 0.0 |
| 22.9 | 7 | 29 | 7 | 24.1 | 1 | 3.4 |
| 25 | 8 | 24 | 5 | 20.8 | 0 | 0.0 |

It is evident from these results that at temperatures ranging from 10° C. to approximately 16° C., the percentage of plantlets that develops a top shoot is lower than at temperatures ranging from approximately 16° C. to 25° C.

It is further evident that at temperatures ranging from 10° C. to approximately 16° C., the percentage of plantlets that develops new white roots is higher than at temperatures ranging from approximately 16° C. to 25° C.

Thus, if both the rooting and the development of a top shoot is to be prioritized, then the most suitable temperature is approximately 14-17° C.

Example 16: Production of *Abies nordmanniana* Christmas Trees

A total of 327 trees from 9 clones of small *Abies nordmanniana* emblings obtained from the method described in Example 6 (i.e. as a result of being developed in accordance with examples 1, 2, 3, 4, 5, wherein the root inducing step comprised growing the somatic embryos at 3-7° C. for 8 to 12 weeks and at the shoot inducing step at light intensities of 150-350 µmol/m²s) were planted in soil in forest in Denmark in areas that were already used for the production of Christmas trees. The appearance and size of the trees were registered regularly. After 8 years of growth in the field, it was concluded that the majority of the trees had survived and the appearance of the trees was compared between the genotypes thereby identifying the genotypes that are most suitable for the production of Christmas trees. It was moreover concluded that trees of the same genotypes were nearly identical of shape and size.

Example 17: Rooting of Fully Mature Somatic Embryos of *Abies nordmanniana* and *Abies bornmülleriana*

In total 3459 fully mature cotyledonary embryos (corresponding to stage 7 as shown in FIG. 1 and in FIG. 2) of the two species *Abies nordmanniana* and *Abies bornmülleriana*, respectively 5 and 2 genotypes, were placed horizontally on rooting medium 51.21 (same recipe as shown in Example 3) in petri dishes comprising 20 embryos per dish. 40-100 embryos of each genotype were grown for 8-11 weeks in the dark at one of the following temperatures, respectively: 2° C., 4° C., 5° C., 8° C., 10° C., 15° C. and 20° C.

Number of embryos employed in experiment by species and genotype:

| Clone | Temperature ° C. | | | | | | | Total clone | Total species |
|---|---|---|---|---|---|---|---|---|---|
|  | 2 | 4 | 5 | 8 | 10 | 15 | 20 | | |
| *Abies nordmanniana* | | | | | | | | | |
| 0.221 | 40 | 60 | 100 | 40 | 40 | 40 | 40 | 360 | |
| 0.690 | 40 | 80 | 120 | 40 | 40 | 40 | 40 | 400 | |
| 0.710 | 40 | 60 | 101 | 40 | 40 | 40 | 40 | 361 | |
| 0.715 | 40 | 59 | 100 | 40 | 40 | 40 | 40 | 359 | |
| 0.721 | 40 | 60 | 100 | 40 | 40 | 40 | 40 | 360 | 1840 |

-continued

| Clone | Temperature ° C. | | | | | | | Total clone | Total species |
|---|---|---|---|---|---|---|---|---|---|
| | 2 | 4 | 5 | 8 | 10 | 15 | 20 | | |
| *Abies bornmülleriana* | | | | | | | | | |
| 0.854 | 40 | 140 | 200 | 40 | 40 | 40 | 40 | 540 | |
| 0.856 | 40 | 79 | 119 | 40 | 40 | 40 | 40 | 398 | 938 |
| Total | 360 | 658 | 1002 | 360 | 360 | 360 | 359 | 3459 | |

After 8, 9, 10 and 11 weeks, the embryos (that had now developed into small plantlets) were checked for root formation and embryos with a well-developed root (longer than 5 mm, such as those shown in FIG. 3) were selected (when the individual embryo first meet the criteria and week of transfer was noted) for further growth under the shoot inducing conditions described in Example 19.

Subject to the shoot inducing conditions described in Example 19, the obtained 'Good emblings' (such as those shown in FIG. 4) were recorded after finalizing step b) and further growing for additional 8 weeks (step c) into well developed emblings of acceptable quality (having at least one rosette of mostly green needles, such as those shown in FIG. 5).

Figure 8:
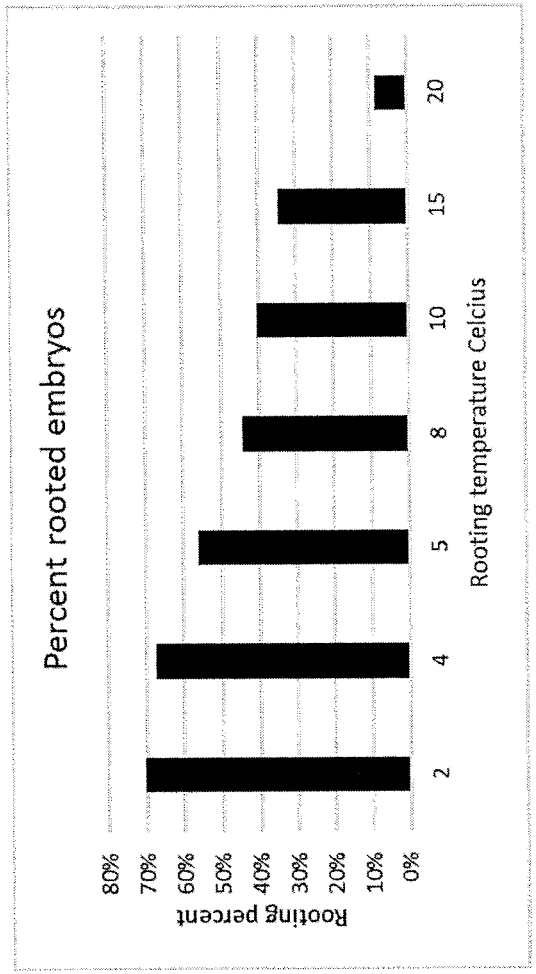
FIG. 8:
Diagram shoving the percentage of rooted embryos of 3459 embryos of *Abies nordmanniana* and *Abies bornmülleriana* that have been grown at 2° C., 4° C., 5° C., 8° C., 10° C., 15° C. or 20° C. in dark for 8 to 11 weeks.

Results:

As shown in FIG. 8, optimum for rooting was found to be between 2-4° C. and rooting was declining with increasing temperature. Strong significant differences in rooting were seen between temperatures. The relationship between rooting and temperature was close to linear ($R^2$=0.94) and rooting drops 7.6 percent-units for an increase in rooting temperature of one degree Celsius. Difference in rooting percent between temperature treatment 2° C. and 4° C. was not significant.

Figure 9:
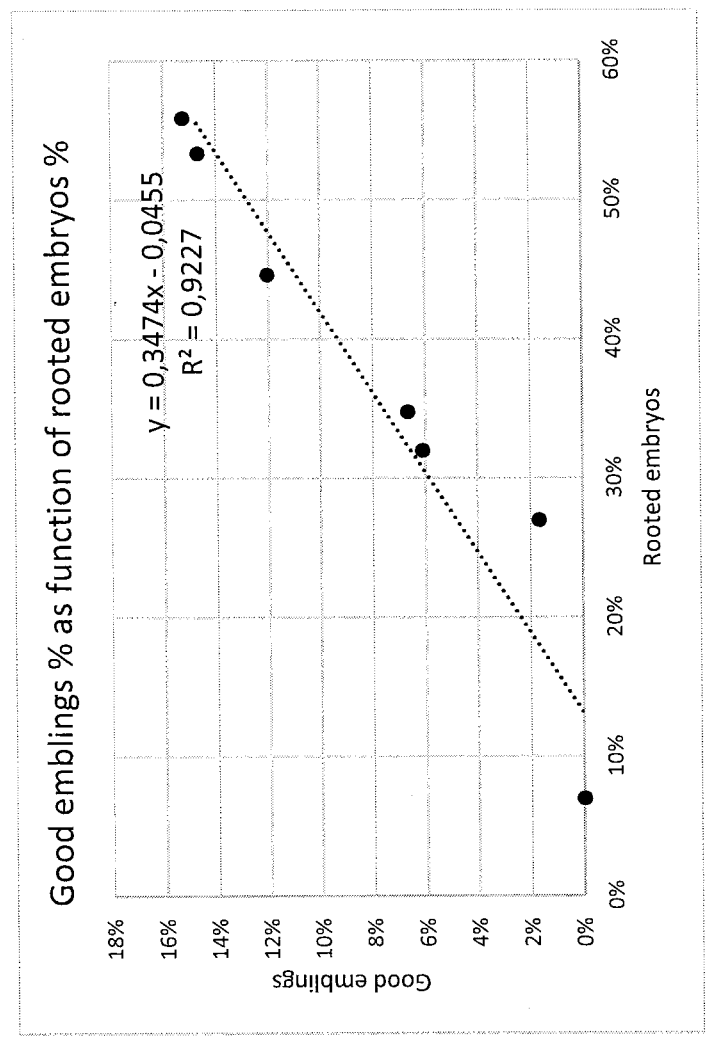
FIG. 9:
Graph showing the percentage of well developed emblings of *Abies nordmanniana* and *Abies bornmülleriana* that have been grown at 2° C., 4° C., 5° C., 8° C., 10° C., 15° C. or 20° C. in dark for 8 to 11 weeks followed by growth in white LED light of 50, 100, 150, 200, 250, 300 and 400 µmol/m²s for 8 weeks at 15° in 24 h light periods followed by additional growth for 8 weeks at 25° C. in white LED light of 175-195 µmol/m²s in 24 h light periods as a function of the percentage of rooted embryos obtained after growth at 2° C., 4° C., 5° C., 8° C., 10° C., 15° C. or 20° C. in dark for 8 to 11 weeks.

Initial rooting has a strong impact (a significant correlation of 0.96) on the final number of good emblings after finalizing step b) (data not shown) and further growing in step c) for additional 8 weeks into well developed emblings of acceptable quality (having at least one rosette of mostly green needles), FIG. 9.

Figure 10:
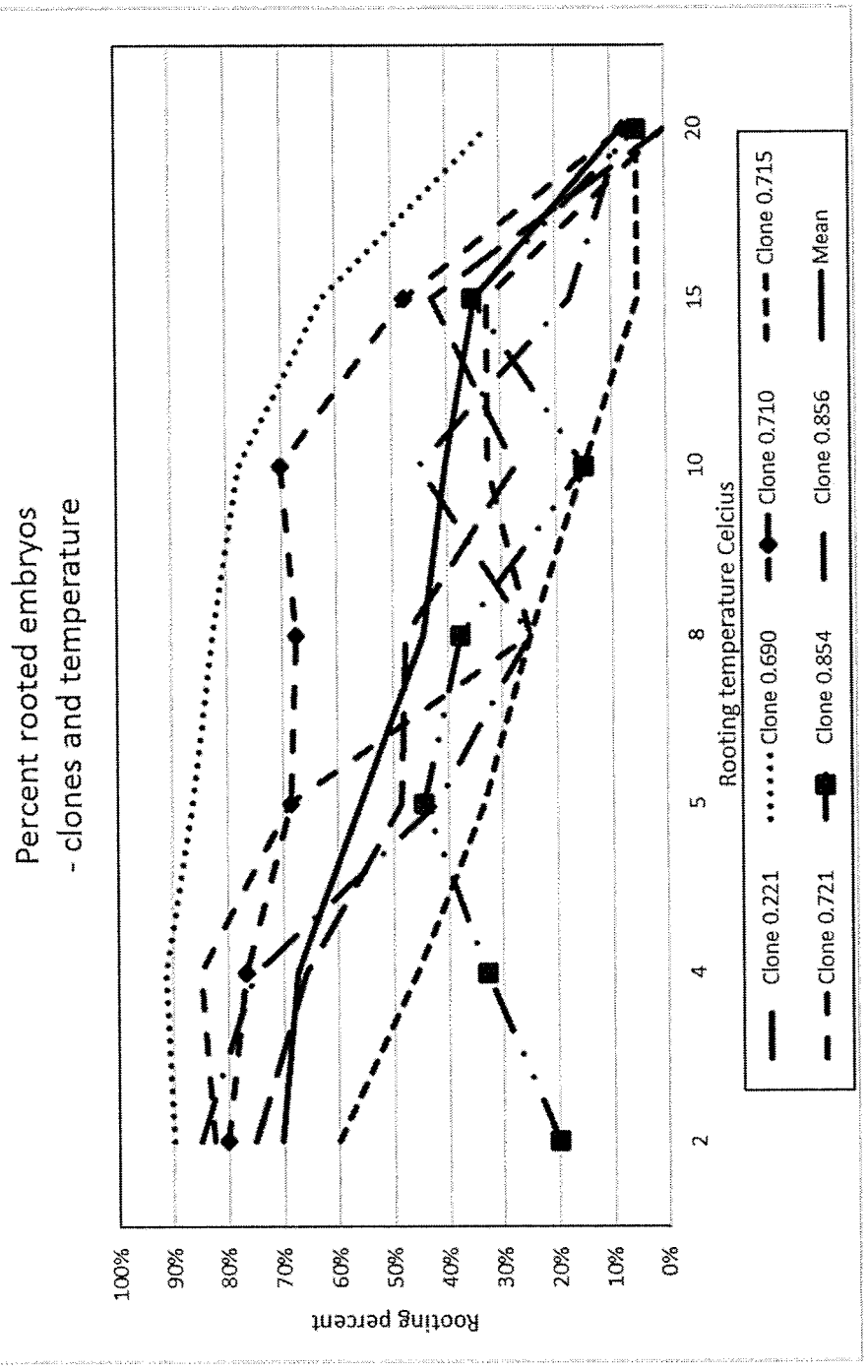
FIG. 10:
Graph showing the percentage of rooted embryos of selected clones of *Abies nordmanniana* and *Abies bornmülleriana* that have been grown at 2° C., 4° C., 5° C., 8° C., 10° C., 15° C. or 20° C. in dark for 8 to 11 weeks.

Significant effect of genotype on rooting was seen. The tested genotypes were in general variable (significant interaction clone by temperature) and showed deviating rooting patterns as function of rooting temperature—some more sensitive to temperature than others, although mostly all clones showed the average pattern of declining rooting by increased temperature, FIG. 10.

Figure 11:
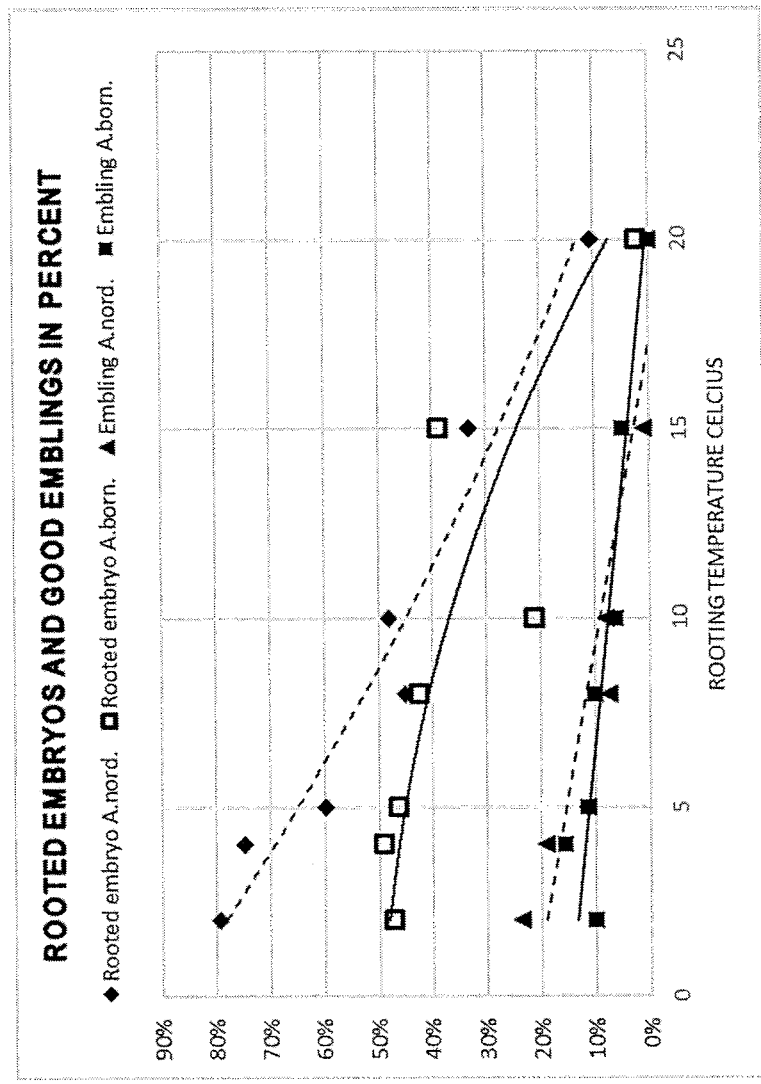
FIG. 11:
Graph showing the percentage of rooted embryos of *Abies nordmanniana* and *Abies bornmülleriana* as a function of the rooting temperature applied (2° C., 4° C., 5° C., 8° C., 10° C., 15° C. or 20° C. in dark for 8 to 11 weeks) in order to obtain the small plantlets; and the percentage of good emblings of *Abies nordmanniana* and *Abies bornmülleriana* obtained as a function of the temperature applied (2° C., 4° C., 5° C., 8° C., 10° C., 15° C. or 20° C. in dark for 8 to 11 weeks) in order to obtain the small plantlets that had subsequently grown in white LED light of 50, 100, 150, 200, 250, 300 or 400 µmol/m²s for 8 weeks at 15° in 24 h light periods followed by additional growth for 8 weeks at 25° C. in white LED light of 175-195 µmol/m²s in 24 h light periods.

The two tested species *Abies nordmanniana* and *Abies bornmülleriana* showed the same general response to temperature in rooting embryos as well as good emblings after finalizing step b) and growing the small emblings in step c) for additional 8 weeks into well developed emblings of acceptable quality, as shown in FIG. 11. Both species were strongly declining with increased temperature, and showing an optimum at 2-5° C.

Figure 12:
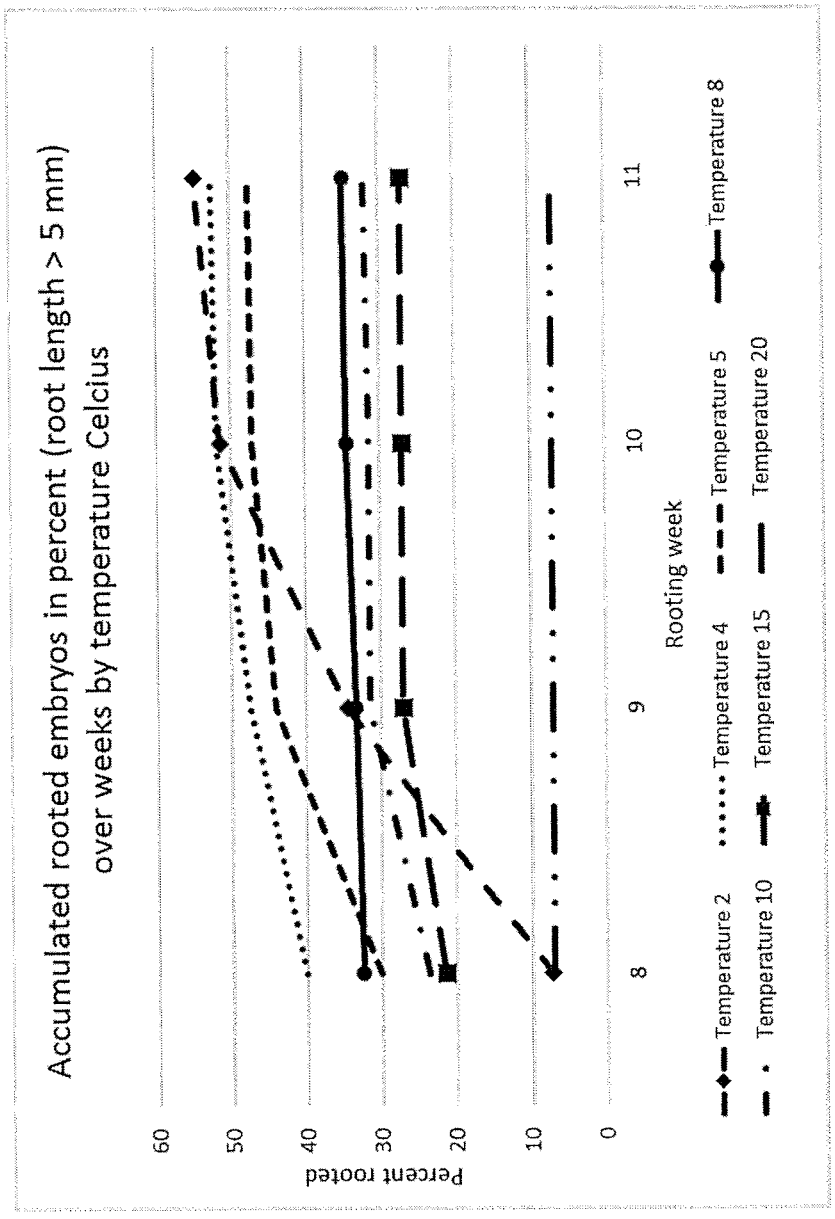
FIG. 12:
Graph showing the percentage of rooted embryos having a root length above 5 mm as a function of the number of weeks subjected to growth in dark at 2° C., 4° C., 5° C., 8° C., 10° C., 15° C. or 20° C., respectively.
Figure 13:
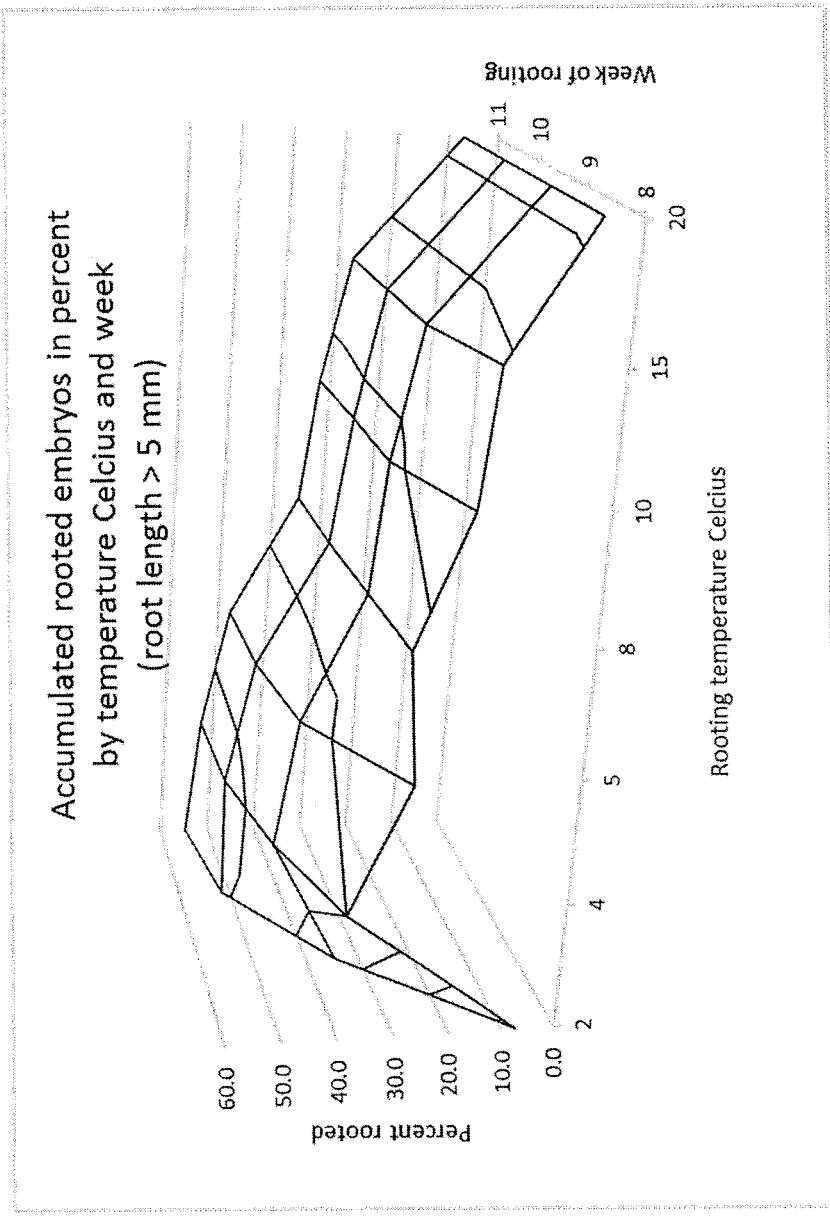
FIG. 13.

The percent of rooted embryos increased in general from week 8 to 11, whereas nearly no new rooting was seen in week 12 and thereafter. The lowest temperatures 2° C., 4° C. and 5° C. had also the steadiest increase in rooted individuals and reached the highest level of accumulated rooting after 11 weeks as shown in FIGS. 12 and 13.

Figure 14:
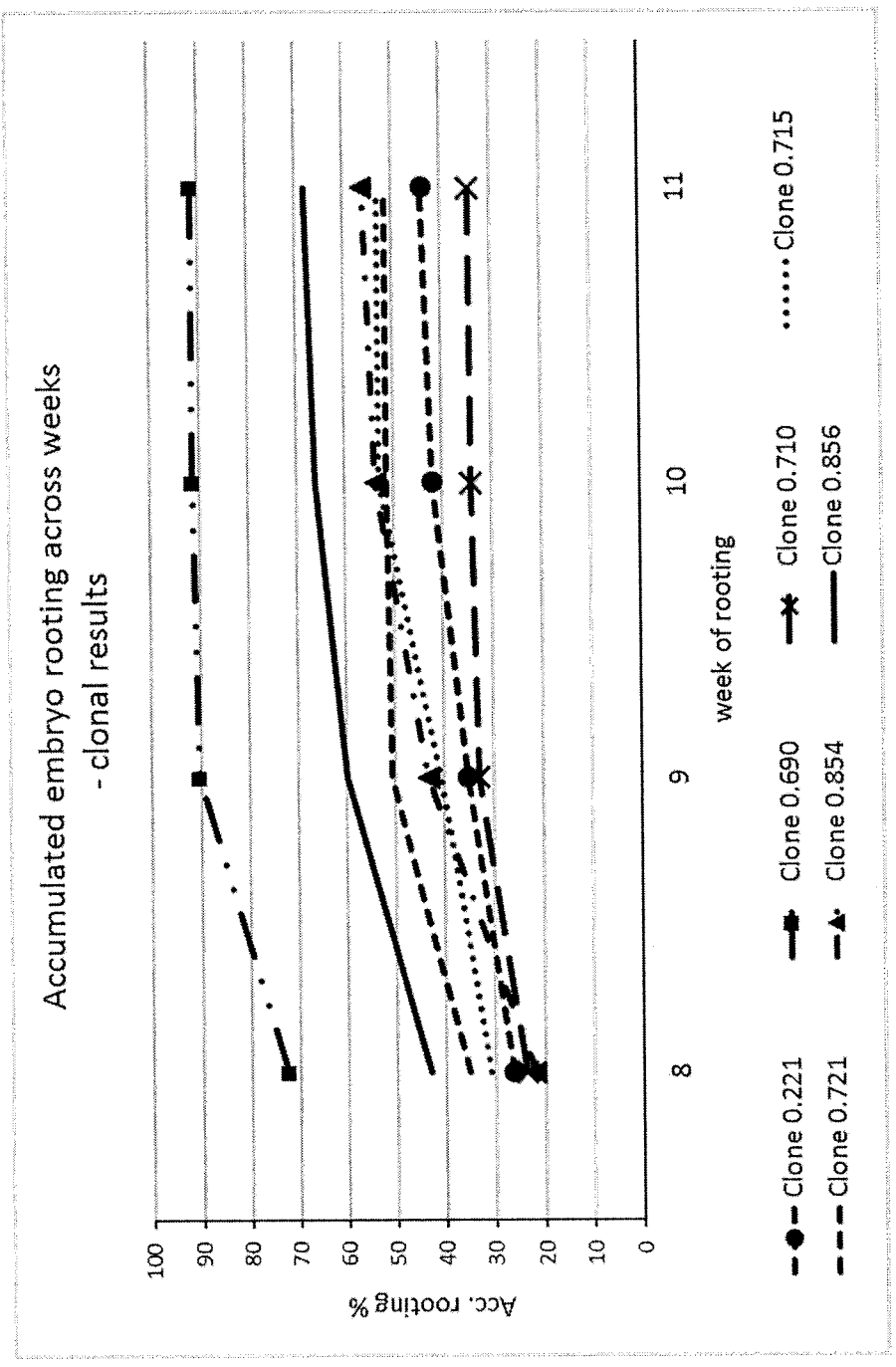

The number of weeks needed to achieve rooting depended also on genotype—at least 9 weeks was needed for some of the tested clones to reach maximum, whereas others benefited from 11 weeks, FIG. 14. Nearly no new rooting was seen in or after week 12.

Examples of suitable small plantlets that were chosen for further growth under shoot inducing conditions are shown in FIG. 3. These small plantlets were characterized in that the cotyledonary embryo had developed a root, the cotyledons were 1-5 mm long, and the hypocotyl was about 5-15 mm long.

Example 18. Rooting of Fully Mature Somatic Embryos of *Abies nordmanniana* and *Abies bornmülleriana*—Effect of Initial Embryo Quality The 3459 fully mature cotyledonary embryos used in Example 17 were prior to any treatment individually evaluated using an initial embryo score assigning a quality score from 4 to 9. Embryos that had obtained scores 1 to 3 were not included in the 3459 embryos selected for growth.

Initial Embryo Quality Score at Time of Initiating Rooting:

Score Description

| | Embryos deformed |
|---|---|
| 1 | Very deformed embryos, embryos accreted, cotyledon's grow from center of hypocotyl, cotyledons deformed |
| 2 | Just long hypocotyl, either straight, bent or shrimp-like |
| 3 | Looks like and embryo, but to many cotyledons, swollen hypocotyl, small and bent |
| | Slightly swollen hypocotyl, minimum 2 cotyledons |
| 4 | hypocotyl less than or equal 1.99 mm |
| 5 | hypocotyle 2.0-3.99 mm |
| 6 | hypocotyle longer or equal 4.0 mm |
| | Slim hypocotyle minimum, 2 cotyledons |
| 7 | hypocotyle less than or equal 3.99 mm |
| 8 | hypocotyle 4.0-5.99 mm |
| 9 | hypocotyle longer or equal 6.0 mm |

After 8, 9, 10 and 11 weeks of growth at the conditions described in Example 17, the embryos were checked for root formation and embryos with a well-developed root (longer than 5 mm) were selected (when the individual embryo first meet the criteria and week of transfer was noted) for further growth under the shoot inducing conditions described in Example 19.

'Good emblings' (such as those shown in FIG. 4) were recorded after finalizing step b) and further growing the small emblings in step c) for additional 8 weeks into well developed emblings of acceptable quality (having at least one rosette of mostly green needles).

Figure 15:
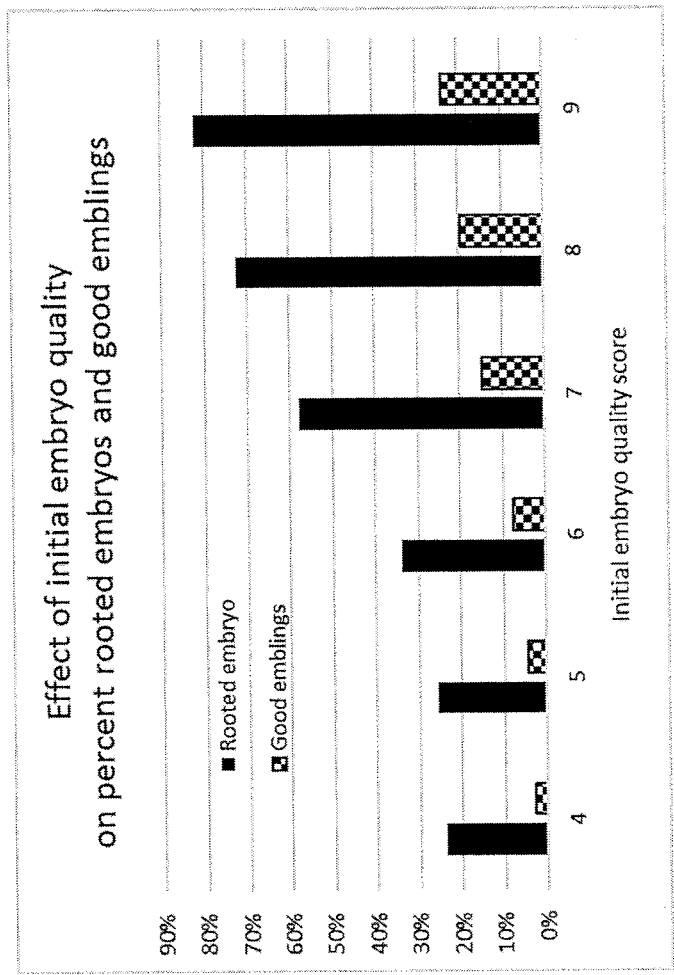

Results:

Percent rooting embryos and percent good emblings increased significantly from embryos having an initial embryo quality score of 4 until 9, respectively a range of rooting from 24 percent to 82 percent and for good emblings 3 percent to 24 percent, FIG. 15.

Figure 16:
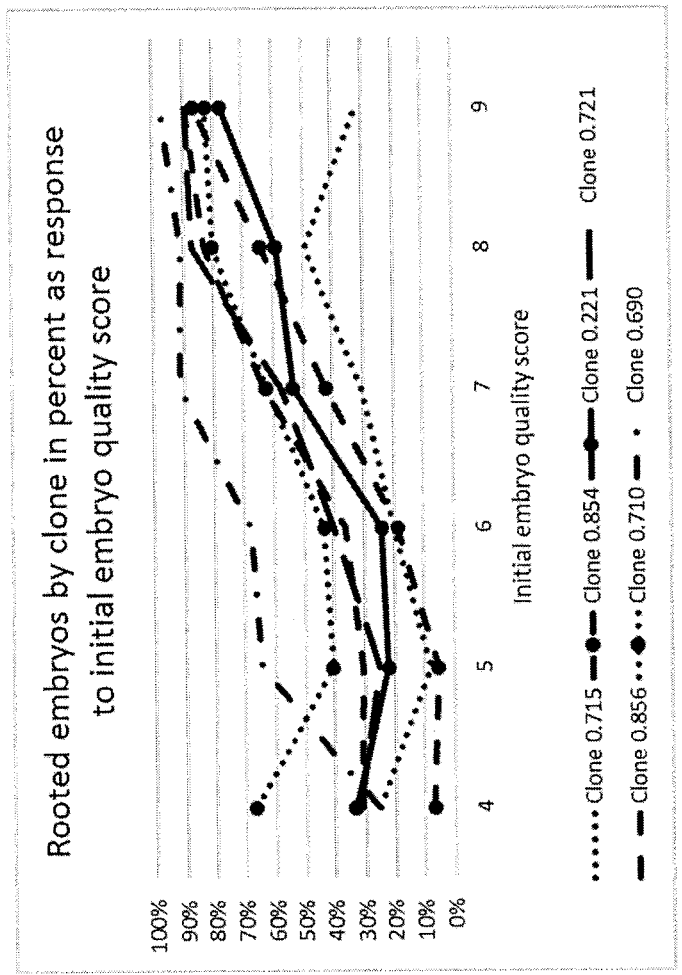

Clones showed some minor deviating patterns in rooting as function of initial embryo score (significant interaction clone by initial embryo score)—although mostly all showed the average pattern of increasing rooting due to increased initial embryo quality, FIG. 16.

Figure 17:
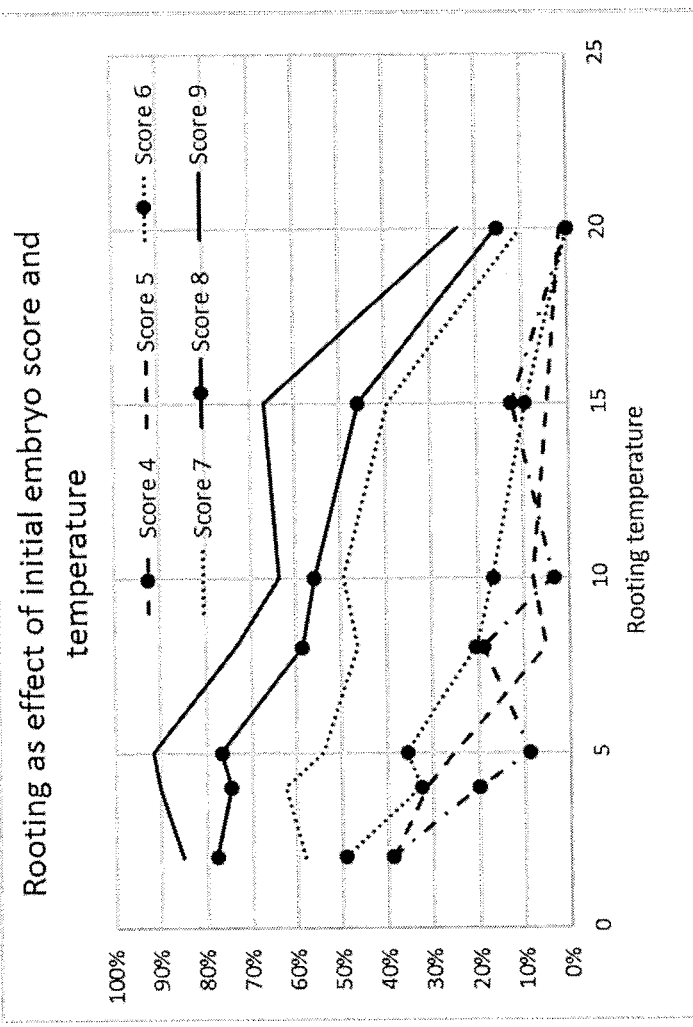

Percent rooting embryos—pooled into groups based on initial embryo scores (scores 4 to 9, respectively) performed very similar across temperatures despite significant interaction (scale effect) between initial rooting score and rooting temperature, FIG. 17.

Example 19: Shoot Development in Rooted Somatic Embryos of *Abies nordmanniana* and *Abies bornmülleriana* Under Light Treatment From the five *Abies nordmanniana* and two *Abies bornmülleriana* genotypes, 1455 small plantlets (of a developmental stage similar to those shown in FIG. 3)—originating from all groups of initial embryo score, that had developed a root when grown under each of the root inducing conditions described in Example 17 were selected for growing under shoot inducing conditions. Most of the selected small plantlets (86 percent) had been grown at 2-6° C. for 8-11 weeks as described in Example 17 since this was the temperature by which most of the somatic embryos successfully developed a root. This group (2-6° C.) accounts only 61 percent of the embryos obtained from Example 17.

| | Score Number of plants per clone and Initial embryo score | | | | | | |
|---|---|---|---|---|---|---|---|
| Clone | 4 | 5 | 6 | 7 | 8 | 9 | Total |
| 0.221 | 1 | 10 | 24 | 67 | 39 | 17 | 158 |
| 0.690 | 8 | 31 | 57 | 117 | 83 | 37 | 333 |
| 0.710 | 4 | 15 | 35 | 83 | 65 | 19 | 221 |
| 0.715 | 1 | 4 | 17 | 33 | 44 | 7 | 106 |
| 0.721 | 9 | 19 | 37 | 41 | 48 | 34 | 188 |
| 0.854 | 4 | 5 | 29 | 58 | 77 | 32 | 205 |
| 0.856 | 17 | 25 | 45 | 77 | 63 | 17 | 244 |
| Total | 44 | 109 | 244 | 476 | 419 | 163 | 1455 |

As mentioned in Example 17, small plantlets selected for being included in this experiment were characterized in having a root, the cotyledons were 1-5 mm long, and the hypocotyl was about 5-15 mm long.

The small plantlets were moved into plastic boxes (Eco2box, oval, Duchefa Bichemie) of 125 mm length×65 mm width×80 mm height having a lid. The lid was partially open for air-movement. The humidity RH % was kept above 90.

Each box contained 100 ml of the sugar-free medium 47.07 (same recipe as shown in Example 3).

As mentioned in Example 17, small plantlets included in this experiment were characterized in having a root. Randomization of this step of the experiment was approximated by transferring rooted embryos from a given clone and petri dish (treatment) into separate boxes. This procedure was repeated during weeks 8 to 11.

At each week, 8-11, boxes were randomized to seven light conditions: of white LED light of 50, 100, 150, 200, 250, 300 and 400 µmol/m²s and were kept at that light condition for 8 weeks at 15° in 24 h light periods.

The light intensities were measured on top of each box as close to the cotyledons as possible, and thereafter accounting for the light reducing effect of the lit. The light intensities ranged from 50 to 400 µmol/m²s depending on the distance from the nearest light source.

Results:

The majority of the small plantlets of both species had developed into emblings having new cotyledons, which also had turned darker green showing a 'normal' surface of a fully developed conifer needle; after 8 weeks. Examples of such emblings are shown in FIG. 4.

Figure 18:
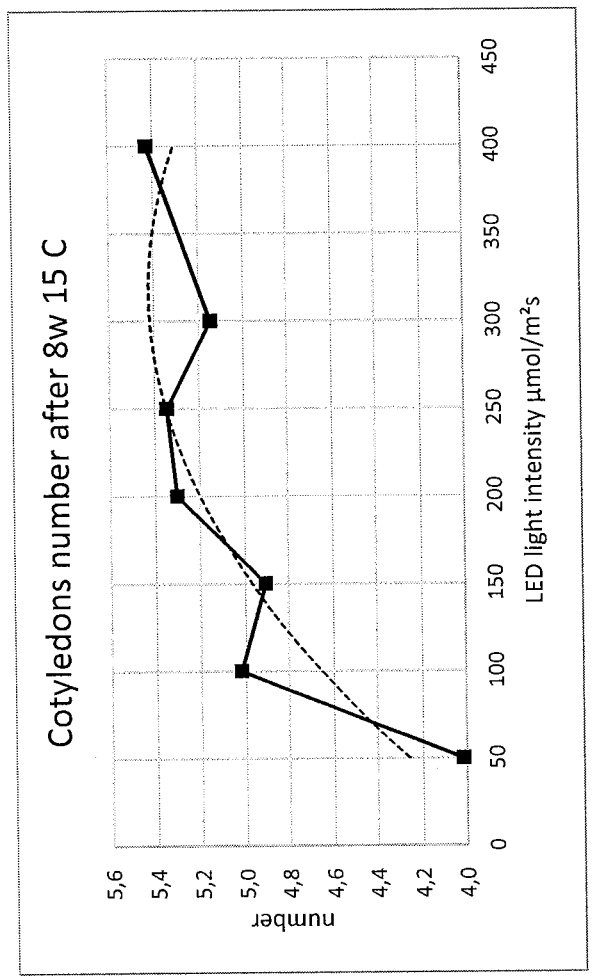

The number of cotyledons developed after 8 weeks varied significantly between light intensities, from 4.0 to 5.4, FIG. 18. A maximum seems to be achieved at 200 µmol/m²s, and no further significant gain in numbers of cotyledons were recorded by further increasing light intensity. The numbers of cotyledons at 50 µmol/m²s was significantly different from the other light intensities.

Figure 19:
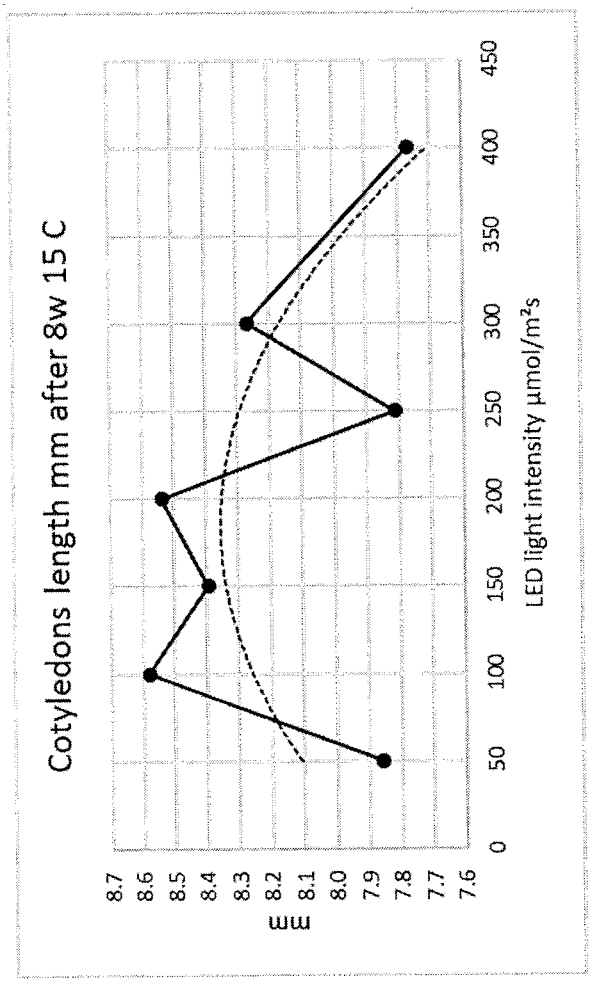

The length of the longest cotyledon on each of the small plantlets were measured after 8 weeks and ranged across light intensities from 7.8 mm to 8.6 mm. The length of the longest cotyledon seems to have a maximum around a light intensity of 100 to 200 µmol/m²s, FIG. 19. The length of the longest cotyledons at an intensity of 100 µmol/m²s and 200 µmol/m²s was both significantly different from the lowest intensity of 50 µmol/m²s, as well as the highest intensity of 400 µmol/m²s.

Example 20: Development of Emblings of *Abies nordmanniana* and *Abies bornmülleriana* Grown in Plugs for 8 Weeks 1455 emblings (of a developmental stage as shown in FIG. 4) that had been grown under root inducing conditions described in Example 17 and subsequently under the shoot inducing conditions as described in Example 19 were selected and transferred to Jiffy7 plugs. Plugs were spiked and watered before transfer of emblings using a solution of NPK fertilizer to a conductivity of 1.5 mS cm-1 and adjusted to a pH of 4.5 using HCl. The plugs containing the small emblings were placed in plastic trays comprising 8 by 13 plugs and covered by a transparent lit. Trays were placed under LED light with an average light intensity of 175-195 µmol/m²s. Room temperature was 25 C. Trays were kept with a lit for six weeks, in week seven lit was slightly raised, and finally removed in week eight. The water content in the plugs was slowly reduced by 14 percent of the initial water content during the 8 weeks. Water was added three days a week.

'Good emblings were recorded after finalizing step b) and further growing the emblings in step c) for additional 8 weeks into well developed emblings of acceptable quality, (i.e. having at least one rosette of mostly green needles.

Figure 20:
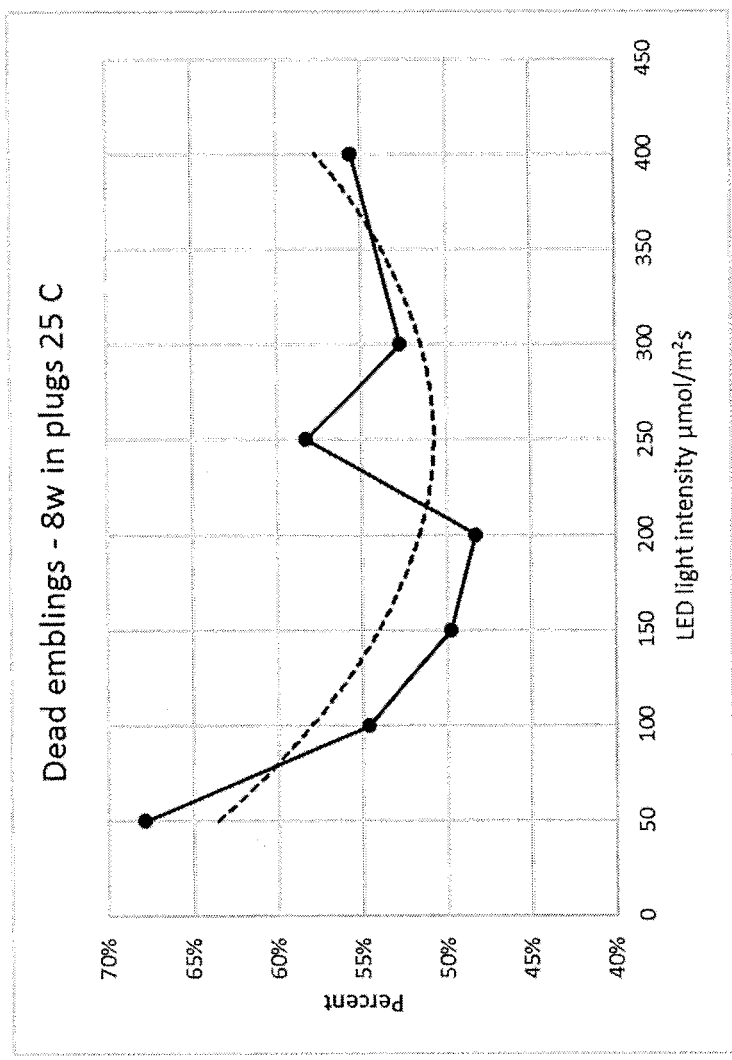

Results:

Although grown under even conditions for eight weeks in standardized plugs, there was a strong and significant effect on mortality due to the previous light treatment as described in Example 19. The mortality was most severe for the plants that had been grown at the lowest light intensity, 50 µmol/m²s, which was significantly different from all other treatments and mortality was at its lowest at a light intensity of 200 µmol/m²s, FIG. 20.

Figure 21:
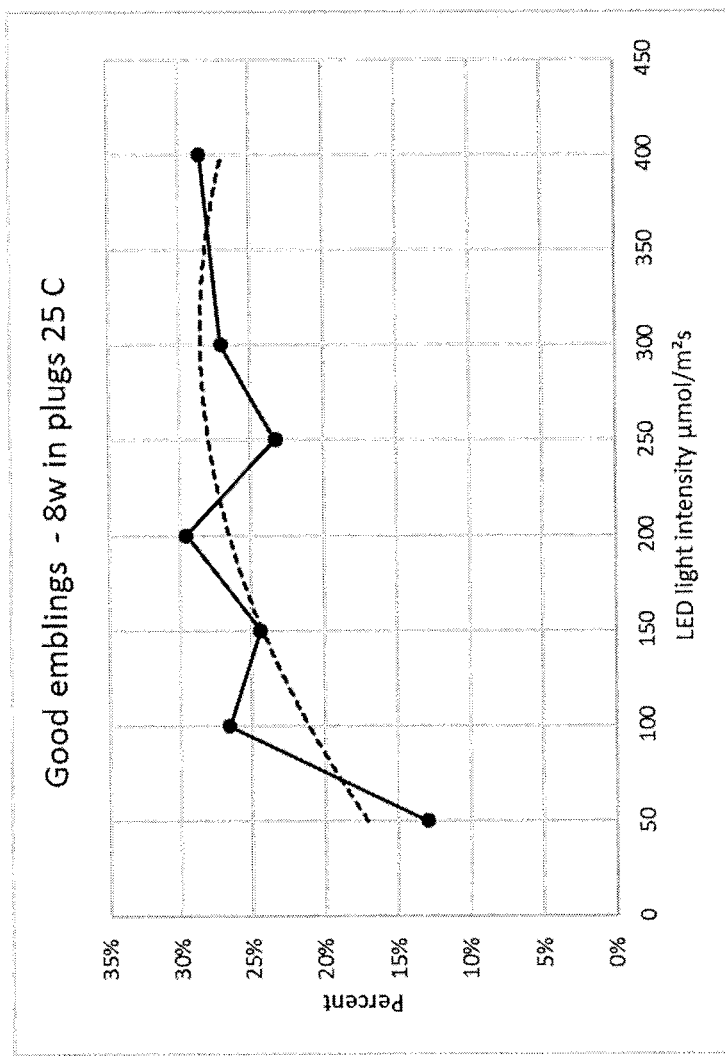

Also for the percentage of good emblings, there was a strong and significant effect of the previous light treatment. Increasing light intensity from 50 µmol/m²s to 200 µmol/ m²s increased the percentage of good emblings from 13 percent to 30 percent, FIG. 21. The light intensity of 50 µmol/m²s was significantly different from all other treatments. No increase in the percentage of good emblings were seen for light intensities above 200 µmol/m²s.

Combining the observed figures for the desired good emblings and realized mortality there is an optimum for the number of good emblings obtained when growing the small plantlets in step b) at 100 to 200 µmol/m²s, with an optimum closest to 200 µmol/m²s.

Figure 22:
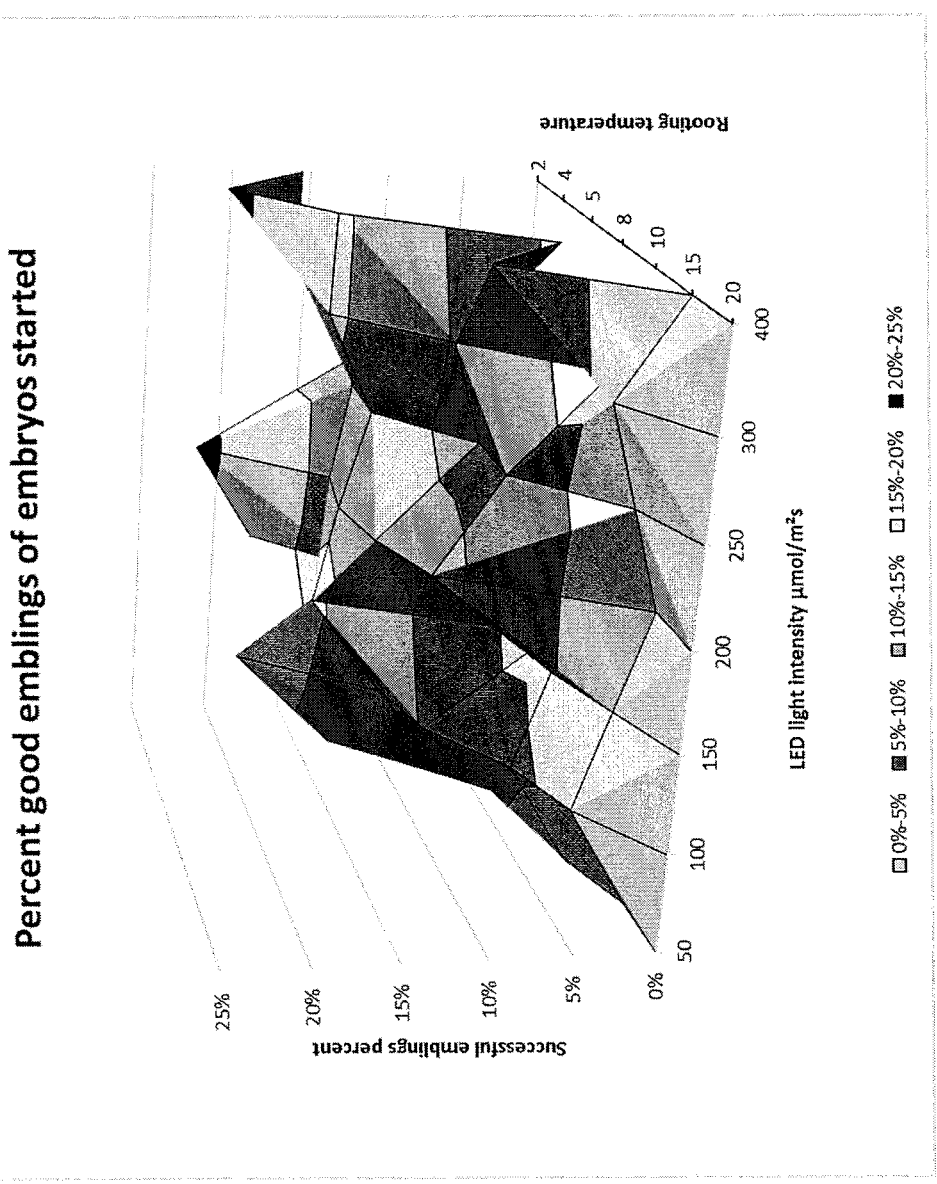

The percent of successful good emblings obtained from the total of embryos started increased with lowering the temperature and showed a maximum in the range of 2° C. to 4° C. in step (a) (the root inducing conditions) and subsequently growing the emblings a LED light intensity of at least 200 µmol/m²s in step (b) (the shoot inducing conditions), as seen in the response surface shown in FIG. 22.

Figure 23:
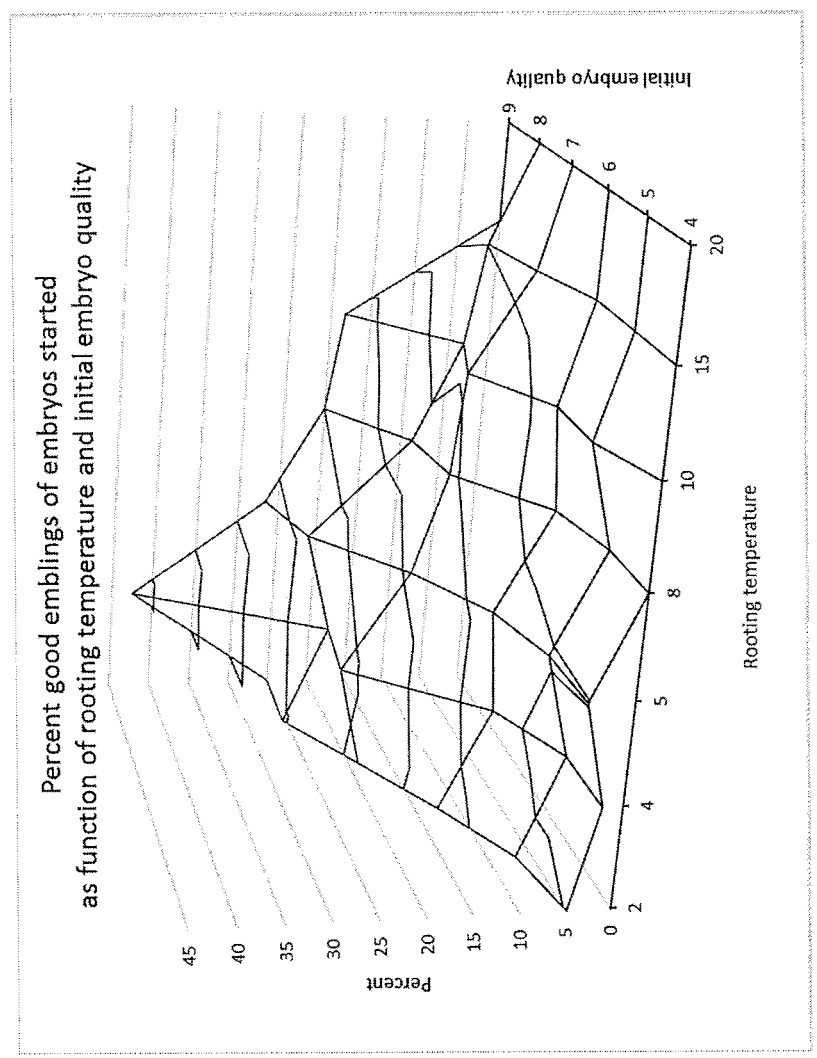

The percent of successful good emblings obtained from the total of embryos started was moreover strongly influenced by the temperature applied in the (a)—the rooting temperature and by the initial embryo quality. Overall, the maximum number of successful good emblings obtained after growth at first the root-inducing conditions and subsequently at the shoot inducing conditions was achieved by growing the fully mature cotyledonary embryos at a temperature of 4° C. and by using embryos having the best initial embryo quality (score 9) as seen in the response surface shown in FIG. 23.

LITERATURE

Farjon and Rushfort, 1989. A classification of *Abies miller* (Pinaceae). Notes of the Royal Botanic Garden Edinburgh 46(1):59-79.

Häggman et al., 1999, Somatic embryogenesis of Scots pine: cold treatment and characteristics of explants affecting induction, Journal of Experimental Botany, Vol. 50, pp. 1769-1778

Liu 1971. A monograph of the genus *Abies*. Taipei, Taiwan: Department of Forestry, College of Agriculture, National Taiwan University.

Malabadi and Nataraja, 2007, Plant Regeneration via Somatic Embryogenesis Using Secondary Needles of Mature Trees of *Pinus roxburghii* Sarg, International Journal of Botany 3, pp. 40-47

Nawrot-Chorabik, 2012, Somatic Embryogenesis in Forest Plants, Chapter 20 in "Embryogenesis", book edited by Ken-ichi Sato, available online on https://www.intechopen.com/books/embryogenesis/somatic-embryogenesis-in-woody-plants Nawrot-Chorabik, 2016, Plantlet regeneration through somatic embryogenesis in Nordmann's fir (*Abies nordmanniana*), J. For. Res. 27, pp. 1219-1228

Nørgaard J V, 1997, somatic embryo maturation and plant regeneration in *Abies nordmanniana* Lk, Plant Science vol 124, pp. 211-22

Pullman et al., 2016, Fraser fir somatic embryogenesis: high frequency initiation, maintenance, embryo development, germination and cryopreservation, New Forests 47, pp. 453-480

US 2009/0280566
U.S. Pat. No. 5,187,092
U.S. Pat. No. 5,731,204
U.S. Pat. No. 6,897,065
von Arnold and Clapham, 2008, Spruce Embryogenesis, Plant Embryogenesis, Volume 427 of the series Methods In Molecular Biology™ pp 31-47 von Arnold et al., Norway spruce as a model for studying regulation of somatic embryo development in conifers, Vegetative Propagation of Forest Trees pp. 351-372 in Somatic Embryogenesis—Fundamental Aspects and Applications. Springer International Publishing 2016

The invention claimed is:

1. A method for development of plants from fully mature somatic embryos of the genus *Abies* comprising:
   a) subjecting fully mature somatic embryos to 2° C.-7° C. for 8-16 weeks;
   b) selecting a small plantlet obtained from step (a) that has developed a root and growing said small plantlet in a substrate that does not comprise a significant concentration of a plant accessible carbohydrate source; at LED light intensities of 70-300 µmol/m²s for at least 3 weeks; and
   c) selecting an embling obtained from step b) and growing the embling into a plant.

2. The method according to claim 1 wherein said temperature in step a) is 3° C.-5° C.

3. The method according to claim 1 wherein said temperature in step a) is 4° C.

4. The method according to claim 1 wherein the fully mature embryos in step a) are subjected to said temperature for 9 to 11 weeks.

5. The method according to claim 1 wherein the fully mature embryos in step a) are subjected to said temperature for 12 weeks.

6. The method according to claim 1 wherein said LED light intensities applied in step b) are 150-250 µmol/m²s.

7. The method according to claim 6 wherein said LED light intensities in step b) are 175-225 µmol/m²s.

8. The method according to claim 1 wherein said small plantlet in step b) is grown in a substrate that does not comprise a significant concentration of a plant accessible carbohydrate source; at said LED light intensities for 4 to 8 weeks.

9. The method according to claim 8 wherein said small plantlet in step b) is grown in a substrate that does not comprise a significant concentration of a plant accessible carbohydrate source; at said LED light intensities for 6 weeks.

10. The method according to claim 1 comprising:
    a) subjecting fully mature somatic embryos to 2° C.-5° C. for 9 to 11 weeks;
    b) selecting a small plantlet from step (a) that has developed a root and growing said small plantlet in a substrate that does not comprise a significant concentration of a plant accessible carbohydrate source; at LED light intensities of 175-225 µmol/m²s for 6 weeks; and
    c) selecting an embling obtained from step b) and growing the embling into a plant.

11. The method according to claim 1 comprising:
    a) subjecting fully mature somatic embryos to 3° C.-7° C. for 12 weeks;
    b) selecting a small plantlet from step (a) that has developed a root and growing said small plantlet in a substrate that does not comprise a significant concentration of a plant accessible carbohydrate source; at LED light intensities of 175-225 µmol/m²s for 6 weeks; and
    c) selecting an embling obtained from step b) and growing the embling into a plant.

12. The method according to claim 1 comprising:
    a) subjecting fully mature somatic embryos to 4° C. for 12 weeks;

b) selecting a small plantlet from step (a) that has developed a root and growing said small plantlet in a substrate that does not comprise a significant concentration of a plant accessible carbohydrate source; at LED light intensities of 200 μmol/m²s for 6 weeks; and
c) selecting an embling obtained from step b) and growing the embling into a plant.

13. The method according to claim 1 wherein said small plantlet in step (b) is grown in a transparent box that allow aeration of said small plantlet.

14. The method according to claim 13 wherein said transparent box comprises a lid having a hole of 10-30% of the total area of the lid.

15. The method according to claim 1 wherein said somatic embryos of the genus *Abies* is selected from: *Abies alba, Abies amabilis, Abies balsamea, Abies beshanzuensis, Abies bifolia, Abies borisii-regis, Abies bornmülleriana, Abies bracteata, Abies cephalonica, Abies chensiensis, Abies cilicica, Abies concolor, Abies delavayi, Abies densa, Abies duragensis, Abies fabri, Abies fargesii, Abies fanjingshanensis, Abies firma, Abies flinckii, Abies forrestii, Abies fraseri, Abies guatemalensis, Abies hickelii, Abies holophylla, Abies homolepis, Abies kawakamii, Abies koreana, Abies lasiocarpa, Abies lowiana, Abies magnifica, Abies mariesii, Abies nebrodensis, Abies nephrolepis, Abies nordmanniana, Abies numidica, Abies pardei, Abies pindrow, Abies pinsapo, Abies procera (Abies nobilis), Abies recurvata, Abies religiosa, Abies sachalinensis, Abies sibirica, Abies spectabilis, Abies squamata, Abies veitchii, Abies vejarii, Abies yuanbaoshanensis, Abies ziyuanensis* or any hybrids obtained from inter-species hybridization between any of these species of the *Abies* genus.

\* \* \* \* \*